US008188011B1

(12) United States Patent
Griffey et al.

(10) Patent No.: US 8,188,011 B1
(45) Date of Patent: May 29, 2012

(54) OPTIMIZATION OF LIGAND AFFINITY FOR RNA TARGETS USING MASS SPECTROMETRY

(75) Inventors: Richard Griffey, Vista, CA (US);
Steven Hofstadler, Oceanside, CA (US);
Jared J. Drader, Encinitas, CA (US);
Kristin S. Lowery, Vista, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 747 days.

(21) Appl. No.: 09/573,479

(22) Filed: May 16, 2000

Related U.S. Application Data

(63) Continuation-in-part of application No. 09/499,875, filed on Feb. 8, 2000, now Pat. No. 6,770,486.

(51) Int. Cl.
*C40B 30/00* (2006.01)
(52) U.S. Cl. .................... 506/9; 436/173; 435/6
(58) Field of Classification Search ............... 435/6, 7.1
See application file for complete search history.

(56) References Cited

U.S. PATENT DOCUMENTS

| 2,648,670 | A | | 8/1953 | Kaiser et al. .................. 260/308 |
| 5,630,243 | A | | 5/1997 | Federico et al. |
| 5,731,424 | A | * | 3/1998 | Toothman et al. ........... 536/23.1 |
| 6,329,146 | B1 | * | 12/2001 | Crooke et al. .................... 435/6 |
| 6,720,190 | B1 | * | 4/2004 | Hindsgaul et al. ................ 506/9 |

FOREIGN PATENT DOCUMENTS

WO  WO 99/45150  9/1999

OTHER PUBLICATIONS

Hofstadler et al. Anal. Chem. (1999) 71:3436-3440.*
Fenn et al., "Electrospray Ionization for Mass Spectrometry of Large Biomolecules", 1989, Science, 246(4929):64-71.*
Fenn et al., "Electrospray Ionization for Mass Spectrometry of Large Biomolecules", 1989, Science, 246(4929), pp. 64-71.*
Loo et al., "Application of electrospray ionization mass spectrometry for studying human immunodeficiency virus protein complexes", 1998, Proteins: Structure, Function, and Genetics, 33(S2), pp. 28-37.*
Joseph A. Loo , "Studying noncovalent protein complexes by electrospray ionization mass spectrometry", 1997, Mass Spectrometry Reviews, vol. 16, Issue 1, p. 1-23.*
Potier et al., "Study of a noncovalent trp repressor: DNA operator complex by electrospray ionization time-of-flight mass spectrometry",1998, Protein Sci, 7(6), pp. 1388-1395.*
Griffey et a., "Targeted Site-Specific Gas-Phase Cleavage of Oligoribonucleotides. Application in Mass Spectrometry-Based Identification of Ligand Binding Sites", Jan. 20, 1999 (Web Published Dec. 29, 1998), Journal of the American Chemical Society , vol. 121, No. 2, pp. 474-475.*
Ni et al., "Collision-induced Dissociation of Polyprotonated Oligonucleotides Produced by Electrospray Ionization", Apr. 1997, Rapid Communications in Mass Spectrometry, vol. 11, Issue 6, pp. 535-540.*
Pramanik et al. "Electrospray Ionization mass Spectrometry for the Study of Non-covalent Complexes: an Emerging Technology" J. Mass Spectrom. 1998, 33, 911-920.*
Benner, W. H. "A Gated Electrostatic Ion Trap to Repetitiously Measure the Charge and M/Z of large Electrospray Ions" Anal. Chem. 1997, 69, 4162-4168.*
Loo, J. A. "Studying Noncovalent protein complexes by electrospray ionization mass spectrometry" mass Spectrometry Reviews 1997, 16, 1-23.*
Cheng et al (1996 PNAS 93:7022-7027).*
Cheng et al [II] (1995 Anal. Chem. 67:586-593).*
Miller et al (1982 Biopolymers 21:633-652).*
Greig et al 1995 JACS 117:10765-10766.*
Loo et al (1997 J. Am. Soc. Mass Spectrom. 8: 234-243).*
Kaur et al (1997 J Protein Chemistry 16:505-511).*
Smith et al (1993 Biol. Mass Spectrometry 22:493-501).*
Amster, I. J., "Fourier Transform Mass Spectrometry," *Jour. of Mass Spectrometry*, 1996, 31:1325-1337.
Anderegg, R. J. et al., "Mass Spectrometric Characterization of a Protein-Ligand Interaction," *J. Am. Chem. Soc.*, 1995, 117, 1374-1377.
Baca, M. et al., "Direct Observation of a Ternary Complex between the Dimeric Enzyme HIV-1 Protease and a Substrate-Based Inhibitor," *J. Am. Chem. Soc.*, 1992, 114, 3992-3993.
Baczynskij et al., "Application of Thermally Assisted Electrospray Ionization Mass Spectrometry for Detection of Noncovalent Complexes of Bovine Serum Albumin with Growth Hormone Releasing Factor and Other Biologically Active Peptides," *Rapid Communications in Mass Spectrometry*, 1994, 8, 280-286.
Bayer, E. et al., "Analysis of Double-Stranded Oligonucleotides by Electrospray Mass Spectrometry", *Anal. Chem.*, 1994, 66, 3858-3863.
Biemann, K., "Mass Spectrometry of Peptides and Proteins," *Ann. Rev. Biochem.*, 1992, 61, 977-1010.
Bowers, M.T. et al., "Mass Spectrometry: Recent Advances and Future Directions," *J. Phys. Chem.*, 1996, 100, 12897-12910.
Bruins, A. P. et al., "Ion Spray Interface for Combined Liquid Chromatography/Atmospheric Pressure Ionization Mass Spectrometry," *Anal. Chem.*, 1987, 59, 2642-2646.
Burlingame, A.L. et al., "Mass Spectrometry," *Anal. Chem.*, 1998, 70, 647R-716R.
Busman, M. et al., "Observation of Large Multimers in the Electrospray Ionization Mass Spectrometry of Peptides," *Rapid Communications in Mass Spectrometry*, 1994, 8, 211-216.
Cai, J. et al., "Capillary electrophoresis-mass spectrometry," *Jour. of Chromatography*, 1995, 703, 667-692.
Cheng, X. et al., "Direct measurement of oligonucleotide binding stoichiometry of gene V protein by mass spectrometry", *Proc. Natl. Acad. Sci USA*, 1996, 93, 7022-7027.
Cheng, X. et al., "Using Electrospray Ionization FTICR Mass Spectrometry to Study Competitive Binding of Inhibitors to Carbonic Anhydrase," *J. Am. Chem. Soc.*, 1995, 117, 8859-8860.

(Continued)

*Primary Examiner* — Christopher M. Gross
(74) *Attorney, Agent, or Firm* — Pepper Hamilton

(57) ABSTRACT

The present invention provides methods for the identification ligand compounds that bind to target molecules such as proteins or structured RNA with as little as millimolar (mM) affinity using mass spectrometry. The methods may be used to determine the mode of binding interaction between two or more of these ligand compounds to the target as well as their relative affinities. Also provided are methods for designing compounds having greater affinity to a target molecule by identifying two or more ligands using mass spectrometry methods of the invention and linking the ligands together to form a novel compound.

26 Claims, 14 Drawing Sheets

OTHER PUBLICATIONS

Cohen, S. L. et al., "Probing the solution structure of the DNA-binding protein Mas by a combination of proteolysis and mass spectrometry," *Protein Science*, 1995, 4, 1088-1099.

Crain et al., "Applications of mass spectrometry to the characterization of oligonucleotides and nucleic acids", *Curr. Opin. Bioetechnol.*, 1998, 9, 25-34.

Doctycz, M. J. et al., "Accumulation and Storage of Ionized Duplex DNA Molecules in a Quadrupole Ion Trap," *Anal. Chem.*, 1994, 66, 3416-3422.

Ens et al., *New Methods for the Study of Biomolecular Complexes, Proceedings of the NATO Advanced Research Workshop*, held Jun. 16-20, 1996, in Alberta, Canada, in NATO ASI Ser., Standing and Chernushevich (eds.), Ser. C, 1998, 510, Kluwer, Dordrecht, Netherlands.

Feng, R. et al., "Analysis of Antibodies and Other Large Glycoproteins in the Mass Range of 150 00-200 000 Da by Electrospray Ionization Mass Spectrometry," *Anal. Chem.*, 1992, 64, 2090-2095.

Fitzgerald, M. et al., "Probing the oligomeric structure of an enzyme by electrospray ionization time-of-flight mass spectrometry", *Proc. Natl. Acad. Sci. USA*, 1996, 93, 6851-6856.

Gale, D. C. et al., "Observation of Duplex DNA-Drug Noncovalent Complexes by Electrospray Ionization Mass Spectrometry," *J. Am. Chem. Soc.*, 1994, 6027-6028.

Ganem, B., "Detection of Oligonucleotide Duplex Forms by Ion-Spray Mass Spectrometry," *Tetrahedron Letts.*, 1993, 34(9), 1445-1448.

Ganem, B., "Detecting Noncovalent Complexes of Biological Macromolecules: New Applications of Ion-Spray Mass Spectrometry," *Chemtracts-Organic Chemistry*, Jan./Feb. 1993, 6, 1-22.

Ganguly et al., "Studies of the *Ras*-GDP and *Ras*-GTP Noncovalent Complexes by Electrospray Mass Spectrometry", *Tetrahedron*, 1993, 49(36), 7985-7996.

Gao, J. et al., "Screening Derivatized Peptide Libraries for Tight Binding Inhibitors to Carbonic Anhydrase II by Electrospray Ionization-Mass Spectrometry," *J. Med. Chem.*, 1996, 39, 1949-1955.

Goodlett, D. R. et al., "Direct Observation of a DNA Quadruplex by Electrospray Ionization Mass Spectrometry," *Biological Mass Spectrometry*, 1993, 22, 181-183.

Greig, M. J. et al., "Measurement of Macromolecular Binding Using Electrospray Mass Spectrometry. Determination of Dissociation Constants for Oligonucleotide-Serum Albumin Complexes," *J. Am. Chem. Soc.*, 1995, 117, 10765-10766.

Griffey et al., "Detection of base pair mismatches in duplex DNA and RNA oligonucleotides using electrospray mass spectrometry", *Proc. SPIE—Int. Soc. Opt. Eng.*, 1997, 2985, 82-86.

Henion, J. et al., "Mass Spectrometric Investigations of Drug-Receptor Interactions," *Therapeutic Drug Monitoring*, 1993, 15, 563-569.

Hu, P. et al., "Determining Calcium-binding Stoichiometry and Cooperativity of Parvalbumin and Calmodulin by Mass Spectrometry," *Jour. of Mass Spectrometry*, 1995, 30, 1076-1082.

Huang, E. et al., "LC/MS and LC/MS/MS Determination of Protein Tryptic Digests," *J. Am. Soc. Mass Spectrom.*, Mar./Apr. 1990, 1(2), 158-165.

Huang, E. C. et al., "Packed-Capillary Liquid Chromatography/Ion-Spray Tandem Mass Spectrometry Determination of Biomolecules," *Anal. Chem.*, 1991, 63, 732-739.

Jensen, O. N. et al., "Direct Observation of UV-crosslinked Protein-Nucleic Acid Complexes by Matrix-assisted Laser Desorption Ionization Mass Spectrometry," *Rapid Communications in Mass Spectrometry*, 1993, 7, 496-501.

Jensen et al., "Mass Spectrometric Characterization of UV-Crosslinked Protein-Nucleic Acid Complexes", *42nd ASMS Conf. on Mass Spectrom. and Allied Topics*, 1994, 923.

Jorgensen et al., "Direct Determination of Solution Binding Constants for Noncovalent Complexes between Bacterial Cell Wall Peptide Analogues and Vancomycin Group Antibiotics by Electrospray Ionization Mass Spectrometry", *Anal. Chem.*, 1998, 70, 4427-4432.

Lane, T. F. et al., "SPARC is a Source of Copper-binding Peptides that Stimulate Angiogenesis," *J. Cell Biology*, May 1994, 125(4), 929-943.

Li, Y.T. et al., "Mass Spectrometric Studies on Noncovalent Dimers of Leucine Zipper Peptides," *J. Am. Chem. Soc.*, 1993, 115, 8409-8413.

Light-Wahl, K. J. et al., "Observation of a Small Oligonucleotide Duplex by Electrospray Ionization Mass Spectrometry," *J. Am. Chem. Soc.*, 1993, 115, 803-804.

Light-Wahl, K. J. et al., "Observation of the Noncovalent Quaternary Associations of Proteins by Electrospray Ionization Mass Spectrometry," *J. Am. Chem. Soc.*, 1994, 116, 5271-5278.

Lim, H. et al., "Recognition of Cell-wall Peptide Ligands by Vancomycin Group Antibiotics: Studies Using Ion Spray Mass Spectrometry," *J. Mass Spectrometry*, 1995, 30, 708-714.

Little, D.P. et al., "Verification of 50- to 100-mer DNA and RNA sequences with high-resolution mass spectrometry," *Proc. Natl. Acad. Sci. USA*, Mar. 1995, 92, 2318-2322.

Loo, J. A., "Studying Noncovalent Protein Complexes by Electrospray Ionization Mass Spectrometry", *Mass Spectrometry Reviews*, 1997, 16, 1-23.

Loo, J.A. et al., "Use of Electrospray Ionization Mass Spectrometry to Probe Antisense Peptide Interactions," *Biological Mass Spectrometry*, 1994, 23, 6-12.

Loo, J.A. et al., "Interaction of Angiotensin Peptides and Zinc Metal Ions Probed by Electrospray Ionization Mass Spectrometry," *J Am. Soc. Mass Spectrom.*, Nov. 1994, 5(11), 959-965.

Loo, J. A., "Bioanalytical Mass Spectrometry: Many Flavors to Choose," *Bioconjugate Chem.*, 1995, 6, 644-665.

Loo, J.A., "Observation of Large Subunit Protein Complexes by Electrospray Ionization Mass Spectrometry," *J. Mass Spectrometry*, 1995, 30, 180-183.

Loo, J.A. et al., Proc. $43^{rd}$ ASMS Conf. on Mass Spectrom. and Allied Topics, 1995.

Marshall, A.G. et al., "Fourier Transform Ion Cyclotron Resonance Mass Spectrometry: The Teenage Years," *Anal. Chem.*, 1991, 63(4), 215A-229A.

Marshall et al., "Fourier Transform Ion Cyclotron Resonance Mass Spectrometry: A Primer", *Mass Spectrom. Rev.*, 1998, 17, 1-35.

Nelson, R. W. et al., "Mass Determination of Human Immunoglobulin IgM Using Matrix-assisted Laser Desorption/Ionization Time-of-flight Mass Spectrometry," *Rapid Communications in Mass Spectrometry*, 1994, 8, 627-631.

Shuker, S. B. et al., *Science*, 1996, 274, 5252, 1531.

Skoog, D.A. et al., "The Mass Spectrometer," in *Principles of Instrumental Analysis*, Second Edition, Saunders College, Philadelphia, PA, 1980, 477-499.

Smith, R.D. et al., "The Observation of Non-covalent Interactions in Solution by Electrospray Ionization Mass Spectrometry: Promise, Pitfalls and Prognosis," *Biological Mass Spectrometry*, 1993, 22, 493-501.

Smith et al., "New mass spectrometric methods for the study of noncovalent associations of biopolymers", *Chem. Soc. Rev.*, 1997, 26, 191-202.

Winger, B.E. et al., "High-Resolution Accurate Mass Measurements of Biomolecules Using a New Electrospray Ionization Ion Cyclotron Resonance Mass Spectrometer," *J. Am. Soc. Mass Spectrom.*, Jul. 1993, 4(7), 566-577.

Witkowska, H. E. et al., "Mass Spectrometric Analysis of a Native Zinc-Finger Structure: The Glucocorticoid Receptor Dna Binding Domain," *J. Am. Chem. Soc.*, 1995, 117(12), 3319-3324.

Berson, S.A., et al., "General principles of radioimmunoassay," *Clin. Chim. Acta*, 1968, 22, 51-69.

Chard, "An introduction to radioimmunoassay and related techniques," *Elsevier Press*, 1982.

Fourmy et al., "Structure of the A Site of *Escherichia coli* 16S Ribosomal RNA Complexed with an Aminoglycoside Antibiotic", *Science*, 1996, 274, 1367-1371.

Georgiadia, M.P., et al., "Synthesis of amino acid derivatives of neamine and 2-deoxystreptamine to be used as mutasynthons," *J. Carbohydr. Chem.*, 1991, 10(5), 739-748.

Greenberg, W.A., et al., "Design and synthesis of new aminoglycoside antibiotics containing neamine as an optimal core structure: correlation of antibiotic activity with in vitro inhibition of translation," *J. Am. Chem. Soc.*, 1999, 121, 6527-6541.

Jonsson, U. et al., "Real-Time Biospecific Interaction Analysis Using Surface Plasmon Resonance and a Sensor Chip Technology," *Biotechniques*, 1991, 11(5), 620-627.

Karlsson, R. et al., "Kinetic analysis of monoclonal antibody-antigen interactions with a new biosensor based analytical system," *Jour. of Immunological Methods*, 1991, 145, 229-240.

Leclerc, F., et al., "MCSS-based predictions of RNA binding sites," *Theor. Chem. Acc.*, 1999, 101, 131-137.

Smith, R.D. et al., "New Developments in Biochemical Mass Spectrometry: Electrospray Ionisation," *Anal Chem.*, 1990, 62, 882-899.

Udenfriend, S., et al., "Scintillation Proximity Assay: A Sensitive and Continuous Isotopic Method for Monitoring Ligand/Receptor and Antigen/Antibody Interactions," *Anal. Biochem.*, 1987, 161, 494-500.

Weiner, S.J., et al., "A new force field for molecular mechanical simulation of nucleic acids and proteins," *J. Am. Chem. Soc.*, 1984, 106, 765-784.

Winger, B.E., et al., "High-resolution accurate mass measurements of biomolecules using a new electrospray ionization ion cyclotron resonance mass spectrometer," *Am. Soc. Mass Spectrometry*, 1993, 566-577.

U.S. Appl. No. 08/678,903.

Dunayevskly, Y.M., et al., "Simultaneous measurement of nineteen binding constants of peptides to vancomycin using affinity capillary electrophoresis-mass spectrometry," *J. Med. Chem.*, 1998, 41, 1201-1204.

Griffey, R.H., et al., "Determinants of aninoglycoside-binding specificity for rRNA by using mass spectrometry," *Proc. Natl. Acad. Sci. USA*, 1999, 96, 10129-10133.

Kempen, E.C., et al., "A method for the determination of binding constants by electrospray ionization mass spectrometry," *Anal. Chem.*, 2000, 72, 5411-5416.

Smith et al., "New mass spectrometric methods for the study of noncovalent associations of biopolymers," *Chemical Society Reviews* (1997) 26:191-202.

European Search Report Dated Oct. 10, 2004 for European Application No. EP 01 92 0970.

Claims of U.S. Appl. No. 09/499,875—Optimization of Ligand Affinity for RNA Targets Using Mass Spectrometry—Inventors: Griffey, Hofstadler, Drader, Lowery, Mohan, filed Feb. 8, 2000.

\* cited by examiner

2-DOS     3,5-DT     2,4-DAP

GA     AICA     4-ABA

2-GBI

OPTIMIZATION OF LIGAND AFFINITY FOR RNA TARGETS USING MASS SPECTROMETRY

CROSS-REFERENCE TO RELATED APPLICATIONS

The present application is a continuation-in-part of U.S. Ser. No. 09/499,875 filed Feb. 8, 2000 (now U.S. Pat. No. 6,770,486), which is incorporated herein by reference in its entirety

FIELD OF THE INVENTION

The present invention is related to mass spectrometry methods for detecting binding interactions of ligands to substrates and in particular to methods for determining the mode of binding interaction of legends to substrates.

BACKGROUND OF THE INVENTION

Drug discovery has evolved from the random screening of natural products into a combinatorial approach of designing large numbers of synthetic molecules as potential bioactive agents (ligands, agonists, antagonists, and inhibitors). Traditionally, drug discovery and optimization have involved the expensive and time-consuming process of synthesis and evaluation of single compounds bearing incremental structural changes. For natural products, the individual components of extracts had to be painstakingly separated into pure constituent compounds prior to biological evaluation. Further, all compounds had to be analyzed and characterized prior to in vitro screening. These screens typically included the evaluation of candidate compounds for binding affinity to their target, competition for the ligand binding site, or efficacy at the target as determined via inhibition, cell proliferation, activation or antagonism end points. Considering all these facets of drug design and screening that slow the process of drug discovery, a number of approaches to alleviate or remedy these matters, have been implemented by those involved in discovery efforts.

The development and use of combinatorial chemistry has radically changed the way diverse chemical compounds are synthesized as potential drug candidates. The high-throughput screening of hundreds of thousands of small molecules against a biological target has become the norm in many pharmaceutical companies. The screening of a combinatorial library of compounds requires the subsequent identification of the active component, which can be difficult and time consuming. In addition, compounds are usually tested as mixtures to efficiently screen large numbers of molecules.

A shortcoming of existing assays relates to the problem of "false positives." In a typical functional assay, a false positive is a compound that triggers the assay but which compound is not effective in eliciting the desired physiological response. In a typical physical assay, a false positive is a compound that attaches itself to the target but in a non-specific manner (e.g. non-specific binding). False positives are particularly prevalent and problematic when screening higher concentrations of putative ligands because many compounds have non-specific affects at those concentrations. Methods for directly identifying compounds that bind to macromolecules in the presence of those that do not bind to the target could significantly reduce the number of "false positives" and eliminate the need for deconvoluting active mixtures.

In a similar fashion, existing assays are also plagued by the problem of "false negatives," which result when a compound gives a negative response in the assay but the compound is actually a ligand for the target. False negatives typically occur in assays that use concentrations of test compounds that are either too high (resulting in toxicity) or too low relative to the binding or dissociation constant of the compound to the target.

When a drug discovery scientist screens combinatorial mixtures of compounds, the scientist will conventionally identify an active pool, deconvolute it into its individual members, and identify the active members via re-synthesis and analysis of the discrete compounds. In addition to false positives and false negative, current techniques and protocols for the study of combinatorial libraries against a variety of biologically relevant targets have other shortcomings. These include the tedious nature, high cost, multi-step character, and low sensitivity of many screening technologies. These techniques do not always afford the most relevant structural and binding information, for example, the structure of a target in solution and the nature and the mode of the binding of the ligand with the receptor site. Further, they do not give relevant information as to whether a ligand is a competitive, noncompetitive, concurrent or a cooperative binder of the biological target's binding site.

The screening of diverse libraries of small molecules created by combinatorial synthetic methods is a recent development that has the potential to accelerate the identification of lead compounds in drug discovery. Rapid and direct methods have been developed to identify lead compounds in drug discovery involving affinity selection and mass spectrometry. In this strategy, the receptor or target molecule of interest is used to isolate the active components from the library physically, followed by direct structural identification of the active compounds bound to the target molecule by mass spectrometry. In a drug design strategy, structurally diverse libraries can be used for the initial identification of lead compounds. Once lead compounds have been identified, libraries containing compounds chemically similar to the lead compound can be generated and used to develop a structural activity relationship (SAR) in order to optimize the binding characteristics of the ligand with the target receptor.

One step in the identification of bioactive compounds involves the determination of binding affinity and binding mode of test compounds for a desired biopolymeric or other receptor. For combinatorial chemistry, with its ability to synthesize, or isolate from natural sources, large numbers of compounds for in vitro biological screening, this challenge is greatly magnified. Since combinatorial chemistry generates large numbers of compounds, often isolated as mixtures, there is a need for methods which allow rapid determination of those members of the library or mixture that are most active, those which bind with the highest affinity, and the nature and the mode of the binding of a ligand to a receptor target.

An analysis of the nature and strength of the interaction between a ligand (agonist, antagonist, or inhibitor) and its target can be performed by ELISA (Kemeny and Challacombe, in *ELISA and other Solid Phase Immunoassays: Theoretical and Practical Aspects*; Wiley, New York, 1988), radioligand binding assays (Berson and Yalow, Clin. Chim. Acta, 1968, 22, 51-60; Chard, in "*An Introduction to Radioimmunoassay and Related Techniques*," Elsevier press, Amsterdam/New York, 1982), surface-plasmon resonance (Karlsson, Michaelsson and Mattson, *J. Immunol. Methods,* 1991, 145, 229; Jonsson et al., *Biotechniques,* 1991, 11, 620), or scintillation proximity assays (Udenfriend, Gerber and Nelson, Anal. *Biochem.,* 1987, 161, 494-500). Radio-ligand binding assays are typically useful only when assessing the competitive binding of the unknown at the binding site for that of the radio-ligand and also require the use of radioactivity. The surface-plasmon resonance technique is more straightforward to use, but is also quite costly. Conventional biochemical assays of binding kinetics, and dissociation and association constants are also helpful in elucidating the nature of the target-ligand interactions but are limited to the analysis of a few discrete compounds.

A nuclear magnetic resonance (NMR)-based method is described in which small organic molecules that bind to proximal subsites of a protein are identified, optimized, and linked together to produce high-affinity ligands (Shuker, S. B.; Hajduk, P. J.; Meadows, R. P.; Fesik, S. W. Science, 1996, 274, 5252, 1531). The approach is called SAR by NMR because structure-activity relationships (SAR) are obtained from NMR. This technique has several drawbacks for routine screening of a library of compounds. For example, the biological target is required to incorporate a $^{15}N$ label. Typically the nitrogen atom of the label is part of amide moiety within the molecule. Because this technique requires deshielding between nuclei of proximal atoms, the $^{15}N$ label must also be in close proximity to a biological target's binding site to identify ligands that bind to that site. The binding of a ligand conveys only the approximate location of the ligands. It provides no information about the strength or mode of binding.

Therefore, methods for the screening and identification of complex target/ligand binding are greatly needed. In particular, new methods are needed for the identification of the strength and mode of binding of a ligand to its intended target.

SUMMARY OF THE INVENTION

This invention provides for methods and processes for identifying weak binding ligands for a target molecule. Ligands are selected that have an affinity for the target molecule that is equal to or greater than a baseline affinity. This can be accomplished according to one embodiment of the invention by utilizing a mass spectrometer and selecting a standard ligand that forms a non-covalent binding complex with the target molecule. An amount of the standard ligand is mixed with an excess amount of the target molecule such that unbound target molecule is present in the mixture. This mixture is introduced into the mass spectrometer and the operating performance conditions of the mass spectrometer are adjusted such that the signal strength of the standard ligand bound to the target molecule is from about 1% to about 30% of the signal strength of unbound target molecule. At least one further ligand is introduced into a test mixture of the target molecule and the standard ligand and this test mixture is introduced into the mass spectrometer. Any complexes of the further ligand and the target wherein the ligand has greater than baseline affinity for the target molecule is identified by discerning the signals that have a signal strength greater than the background noise of the mass spectrometer.

The invention further provides for methods and processes for selecting those members of a group of compounds that can form a non-covalent complex with a target molecule and where the affinity of the members for the target molecule is greater than a baseline affinity. This can be accomplished by utilizing a mass spectrometer and selecting a standard compound that forms a non-covalent binding complex with the target molecule. An amount of the standard compound is mixed with an excess amount of the target molecule such that unbound target molecule is present in the mixture and the mixture is introduced into the mass spectrometer. The operating performance conditions of the mass spectrometer are adjusted such that the signal strength of the standard compound bound to the target molecule is from about 1% to about 30% of signal strength of unbound target molecule. Next a sub-set of the group of compounds is introduced into a test mixture of the target molecule and standard compound and this test mixture is introduced into the mass spectrometer. Those members of the sub-set of compounds that form complexes with the target with an affinity greater than baseline are identified by discerning those signals that have a signal strength greater than the background noise of the mass spectrometer. The individual members are then identified by their respective molecular masses.

The invention further includes methods and processes for determining the relative interaction between at least two ligands with respect to a target substrate. This is accomplished by mixing an amount of each of the ligands with an amount of the target substrate to form a mixture. The mixture is then analyzed using mass spectrometry to determine the presence or absence of a ternary complex corresponding to simultaneous binding of two of the ligands with the target substrate. The absence of a ternary complex in the mixture indicates that binding of the ligands to the target is competitive while the presence of a ternary complex indicates that binding of the ligands is other than competitive.

The invention further includes methods and processes for determining the binding interaction of ligands to a target substrate. This is accomplished by mass spectrometry analysis of the mixture as described to determine if the binding is other than competitive followed by determination of the ion abundance of i) a ternary complex present in the mixture, ii) a first binary complex corresponding to the adduction of a first ligand with the target substrate; iii) a second binary complex corresponding to the adduction of a second ligand with the target substrate; and iv) target substrate unbound or not complexed with either of the first or second ligands. The absolute ion abundance of the ternary complex is compared to the sum of the relative ion abundance of the binary complexes which contribute to the formation of the ternary complex. The relative ion abundance of one of the contributing binary complexes is calculated by multiplying the absolute ion abundance of the first binary complex with the relative ion abundance of the second binary complex with respect to the unbound target substrate. The relative ion abundance of the second binary complex is calculated by dividing that binary complex absolute ion abundance by the absolute ion abundance of the unbound target. Similarly, the relative ion abundance of the other contributing binary complex is calculated by multiplying the absolute ion abundance of the second binary complex with the relative ion abundance of the first binary complex.

If the absolute ion abundance of the ternary complex is equal to the sum of the relative ion abundances of the contributing binary complexes this indicates concurrent binding interaction of the ligands to the target substrate. If the absolute ternary complex ion abundance is greater this indicates cooperative binding interaction, and if lesser this indicates competitive binding interaction.

The invention further includes methods and processes for determining the relative proximity of binding sites of a first and a second ligand on a target substrate. This can be accomplished by exposing the target substrate to a mixture of the second ligand and a plurality of derivative compounds of the first ligand. Each of the first ligand derivatives has the chemical structure of the first ligand and at least one substituent group pending from it or if the first ligand includes a ring within its structure, derivatives of the ligand can include expansion of contraction of that ring. This mixture is analyzed by mass spectrometry to identify a first ligand derivative that inhibits the binding of the second ligand to the target substrate or visa versa, i.e. binds competitively with the second ligand as determined by the absence of a ternary complex corresponding to the simultaneous complexation of the first ligand derivative and the second ligand with the target.

This invention further provides for methods and processes for determining the relative orientation of a first ligand to a second ligand when these ligands are bound to a target substrate. This is accomplished by exposing the target substrate to a mixture of the second ligand and a plurality of derivative compounds of the first ligand. Each of the first ligand derivatives has the chemical structure of the first ligand and a substituent group pending therefrom. The mixture is analyzed by mass spectrometry to identify a first ligand derivative that inhibits the binding of the second ligand to the target substrate or visa versa, i.e. binds competitively with the second ligand as determined by the absence of a ternary complex corresponding to the simultaneous complexation of the first ligand derivative and the second ligand with the target.

This invention further provides for a screening method for determining compounds that have binding affinity to a target substrate. This is accomplished using mass spectrometry to identifying two ligands that bind to a target non-competitively in a mixture of the ligands and target substrate. These two ligands are then concatenated to form another ligand that has greater binding affinity for the target substrate than either of the two ligands.

The invention further includes methods and processes for modulating the binding affinity of ligands for a target molecule. This is accomplished by selecting a first ligand fragment and a second ligand fragment and then exposing a target molecule to these ligand fragments. The target molecule exposed to the ligand fragments is then interrogated in a mass spectrometer to identify binding of the ligand fragments to the target molecules. The ligand fragments are concatenated together in a structural configuration that improves the binding properties of the fragments for the target molecule.

The invention further includes methods and processes for refining the binding of ligands to target molecules. This is accomplished by selecting first and second virtual fragments of a ligand followed by virtually concatenating the selected ligand fragments together in silico to form a 3D model of the concatenated ligand fragments. This 3D model of the concatenated ligand fragments is then positioned in silico on a 3D model of the target molecule. The various in silico positions of the 3D model of the concatenated ligand fragments on the in silico 3D model of the target molecule are scored. Using the results of the scoring, the in silico position of the 3D model of the concatenated ligand fragments on the in silico 3D model of the target molecule is refined. In a preferred embodiment of this method, real ligand fragments corresponding to the virtual ligand fragments are concatenated together to covalently join these ligand fragments into a new molecule. The new molecule is mixed with a target molecule and the mixture interrogated in the mass spectrometer for binding of the new molecule to the target molecule.

In each of the above methods and processes, in a preferred embodiment, an electrospray mass spectrometer is utilized. Preferred electrospray ionization is accomplished by Z-spray, microspray, off-axis spray or pneumatically assisted electrospray ionization. Further countercurrent drying gas can be used. Preferred mass analyzers for use in identifying the complexes are quadrupole, quadrupole ion trap, time-of-flight, FT-ICR and hybrid mass detectors. The preferred method of measuring signal strength is by the relative ion abundance. The mass spectrometer can also include a gated ion storage device for effecting thermolysis of the test mixtures within the mass spectrometer.

Adjustment of the mass spectrometer operating performance conditions would include adjustment of the source voltage potential across the desolvation capillary and a lens element of the mass spectrometer. This is best monitored by ion abundance of free target molecule. Adjustment of the mass spectrometer operating conditions further can include adjustment of the temperature of the desolvation capillary and adjustment of the operating gas pressure with the mass spectrometer downstream of the desolvation capillary.

In a preferred embodiment, adjustment of the operating performance conditions of the mass spectrometer is effected by adjustment of the voltage potential across the desolvation capillary and a lens element to generate an ion abundance of the ion from a complex of standard ligand with the target of from about 1% to about 30% compared to the abundance of the ion from the target molecule. A more preferred range of abundance of the complex of standard ligand with target to the abundance of the ion from the target molecule is from about 10% to about 20%.

Preferred for standard ligands are those ligands having a baseline affinity for the target of about 10 to about 100 millimolar. Particularly preferred are standard ligands having a baseline affinity for the target molecule of about 50 millimolar as expressed as a dissociation constant. Particularly preferred for standard ligands for nucleic acid targets are amines, primary, secondary or tertiary, amino acids, and nitrogen containing heterocycles with ammonium being the most preferred. Particularly preferred for standard ligands for peptides are esters, phosphates, borates, amino acid and nitrogen containing heterocycles.

The target molecule can be one of various target molecules including RNA, DNA, proteins, RNA-DNA duplexes, DNA duplexes, polysaccharides, phospholipids and glycolipids. Preferred are nucleic acids and proteins with RNA being particularly preferred as a target molecule.

Various RNA molecules are useful as the target. Preferred RNA target molecules are those that are fragments of larger RNA molecules including those being from about 10 to about 200 nucleotides in length. A more preferred RNA target is RNA of from about 15 to about 100 nucleotides in length including those having secondary and ternary structure.

Preferred ligand molecules include those having a molecular mass of less than about 1000 Daltons and fewer that 15 rotatable bonds, i.e., covalent bonds linking one atom to a further atom in the molecule and subject to rotation of the respective atoms about the axis of the bond. More preferred ligands molecules include those having a molecular mass of less than about 600 Daltons and fewer than 8 rotatable bonds. Even more preferred ligand molecules include those have a molecular mass of less than about 200 Daltons and fewer than 4 rotatable bonds. Further preferred ligands include those having no more than one sulfur, phosphorous or halogen atom.

The ligands can comprise members of collection libraries. Preferred collection libraries include historical repositories of compounds, collections of natural products, collections of drug substances or intermediates for such drug substances, collections of dyestuffs, commercial collections of compounds or combinatorial libraries of compounds. A preferred collection for selecting ligands can contain various numbers of members with libraries of from 2 to about 100,000 being preferred.

DESCRIPTION OF PREFERRED EMBODIMENTS OF THE INVENTION

Figure 1:
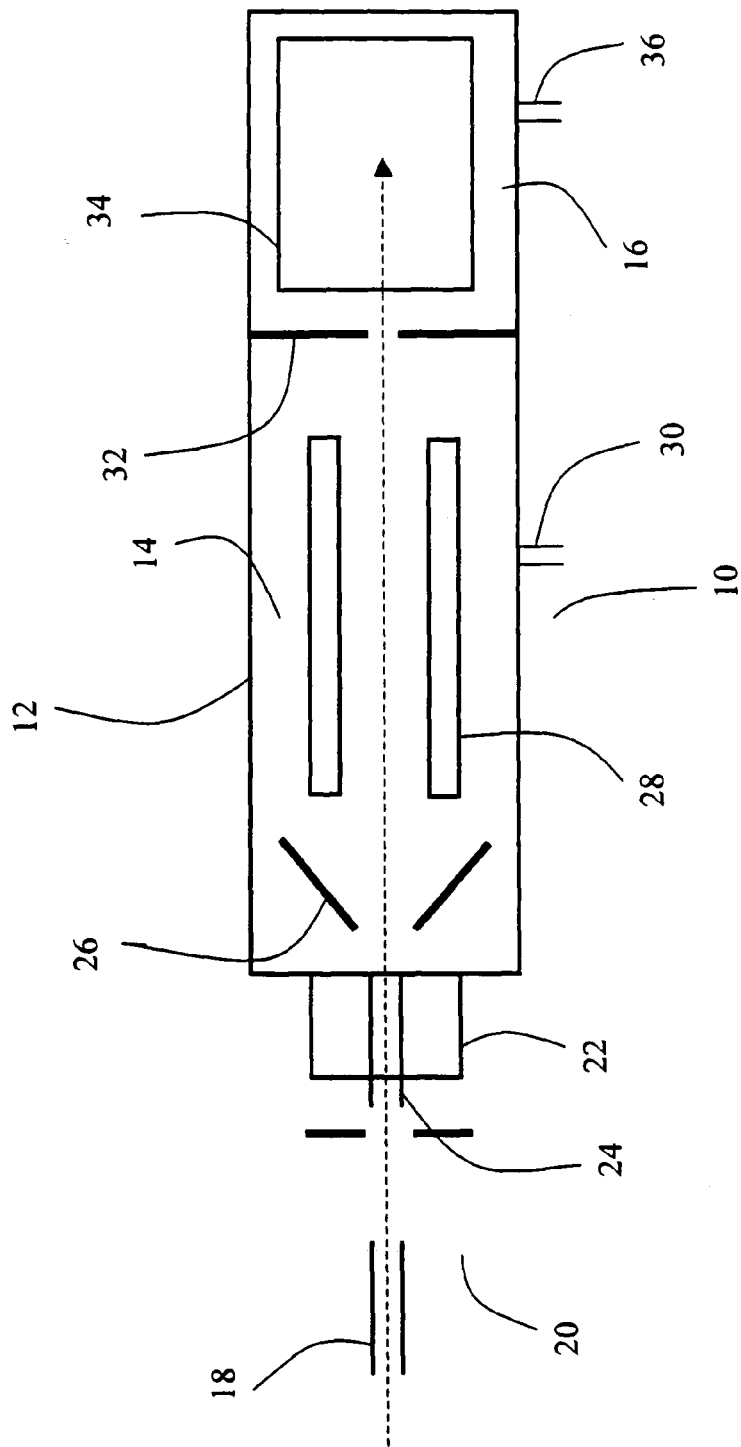
FIG. 1 is a schematic representation of a mass spectrometer employing an electospray ion source.

The methods of the present invention are useful for the detection, evaluation and optimization of ligands to targets especially biological targets. The methods and processes of the invention utilize mass spectrometry as the primary tool to accomplish this. The detection and evaluation of the different binding modes of noncovalently bound ligands to a target are useful for advancing the structure activity relationship (SAR) and for designing ligands with higher binding affinities for their given target sites.

Mass spectrometry has been used to afford direct and rapid methods to identify lead compounds and to study the interactions between small molecules and biological targets. An advantage of mass spectrometry in identifying lead compounds is the sensitivity of the detection process. Small molecules (ligands) which bind to a target through weak noncovalent interactions, may be missed through conventional screening assays. These noncovalent ligand:target complexes, however, are readily detected by mass spectral analysis using the methods and processes of the invention.

These small molecules include both tight and weak binding ligands that bind to a particular target. In both collections of compounds and in biological samples, tight binding ligands can be present in very low concentrations relative to the weaker binding ligands. A tight binding ligand may be part of a very large library of compounds (e.g. a combinatorial library) or may be present in trace amounts of a tissue extract. In both cases, there is usually a much higher concentration of weaker binding ligands relative to the tight binding ligands.

A tight or a weak binding ligand can bind to a target by a noncovalent bond. These noncovalent interactions include hydrogen-bonding, electrostatic, and hydrophobic contacts that contribute to the binding affinity for the target. The difference between a tight and weak binding ligand is relative, a tight binding ligand has a stronger interaction between a target than does a weak binding ligand. Tight and weak binding noncovalent complexes are in equilibrium with the free ligand and free target. If a target is incubated with a mixture of two ligands, e.g., a tight binding and a weak binding ligand, an equilibrium will be established between the bound and unbound forms of each ligand with the binding site of the biological target. At equilibrium, an equilibrium constant (binding constant) can be calculated and is used as a measure of the binding affinities of the ligands. Binding affinity is a measure of the attraction between a ligand and its target.

A binding site is the specific region of a target where a substrate or a ligand binds to form a complex. For example, an enzyme's active site is where catalysis takes place. In a structured RNA molecule, binding of a ligand at a binding site can result in the disruption of the transcription or translation processes. A ligand is a small molecule that binds to a particular large molecule, a target molecule. Typically the target molecule is a large molecule, as for instance, a biological target such as a protein (enzyme) or a structured RNA or DNA.

A preferred target molecule is RNA particularly structured RNA. Structured RNA is a term that refers to definable, relatively local, secondary and tertiary structures such as hairpins, bulges, internal loops, junctions and pseudoknots. Structured RNA can have both base paired and single stranded regions. RNA can be divided into primary, secondary, and tertiary structures and is defined similarly to proteins. Thus the primary structure is the linear sequence. The secondary structure reflects local intramolecular base pairing to form stems and single stranded loops, bulges, and junctions. The tertiary structure reflects the interactions of secondary structural elements with each other and with single stranded regions.

Mass spectrometry (MS) is a powerful analytical tool for the study of molecular structure and interaction between small and large molecules. The current state of the art in MS is such that sub-femtomole quantities of material can be readily analyzed to afford information about the molecular contents of the sample. An accurate assessment of the molecular weight of the material may be quickly obtained, irrespective of whether the samples' molecular weight is several hundred, or in excess of a hundred thousand, atomic mass units or Daltons (Da). It has now been found that mass spectrometry can elucidate significant aspects of important biological molecules. One reason for the utility of MS as an analytical tool is the availability of a variety of different MS methods, instruments, and techniques that can provide different pieces of information about the samples.

A mass spectrometer analyzes charged molecular ions and fragment ions from sample molecules. These ions and fragment ions are then sorted based on their mass to charge ratio (m/z). A mass spectrum is produced from the abundance of these ions and fragment ions that is characteristic of every compound. In the field of biotechnology, mass spectrometry has been used to determine the structure of a biomolecule, as for instance determining the sequence of oligonucleotides, peptides, and oligosaccharides.

In principle, mass spectrometers consist of at least four parts: (1) an inlet system; (2) an ion source; (3) a mass analyzer; and (4) a mass detector/ion-collection system (Skoog, D. A. and West, D. M., Principles of Instrumental Analysis, Saunders College, Philadelphia, Pa., 1980, 477-485). The inlet system permits the sample to be introduced into the ion source. Within the ion source, molecules of the sample are converted into gaseous ions. The most common methods for ionization are electron impact (EI), electrospray ionization (ESI), chemical ionization (CI) and matrix-assisted laser desorption ionization (MALDI). A mass analyzer resolves the ions based on mass-to-charge ratios. Mass analyzers can be based on magnetic means (sector), time-of-flight, quadrupole and Fourier transform mass spectrometry (FTMS). A mass detector collects the ions as they pass through the detector and records the signal. Each ion source can potentially be combined with each type of mass analyzer to generate a wide variety of mass spectrometers.

Mass spectrometry ion sources are well known in the art. Two commonly used ionization methods are electrospray ionization (ESI) and matrix-assisted laser desorption/ionization (MALDI) (Smith et al., Anal. Chem., 1990, 62, 882-899; Snyder, in Biochemical and Biotechnological Applications of Electrospray Ionization Mass Spectrometry, American Chemical Society, Washington, D.C., 1996; and Cole, in Electrospray Ionization Mass Spectrometry: Fundamentals, Instrumentation, Wiley, New York, 1997).

ESI is a gentle ionization method that results in no significant molecular fragmentation and preserves even weakly bound complexes between biopolymers and other molecules so that they are detected intact with mass spectrometry. ESI produces highly charged droplets of the sample being studied by gently nebulizing a solution of the sample in a neutral solvent in the presence of a very strong electrostatic field. This results in the generation of highly charged droplets that shrink due to evaporation of the neutral solvent and ultimately lead to a "coulombic explosion" that affords multiply charged ions of the sample material, typically via proton addition or abstraction, under mild conditions.

Electrospray ionization mass spectrometry (ESI-MS) is particularly useful for very high molecular weight biopolymers such as proteins and nucleic acids greater than 10 kDa in mass, for it affords a distribution of multiply-charged molecules of the sample biopolymer without causing any significant amount of fragmentation. The fact that several peaks are observed from one sample, due to the formation of ions with different charges, contributes to the accuracy of ESI-MS when determining the molecular weight of the biopolymer because each observed peak provides an independent means for calculation of the molecular weight of the sample. Averaging the multiple readings of molecular weight obtained from a single ESI-mass spectrum affords an estimate of molecular weight that is much more precise than would be obtained if a single molecular ion peak were to be provided by the mass spectrometer. Further adding to the flexibility of ESI-MS is the capability of obtaining measurements in either the positive or negative ionization modes.

ESI-MS has been used to study biochemical interactions of biopolymers such as enzymes, proteins and macromolecules such as oligonucleotides and nucleic acids and carbohydrates and their interactions with their ligands, receptors, substrates or inhibitors (Bowers et al., Journal of Physical Chemistry, 1996, 100, 12897-12910; Burlingame et al., J. Anal. Chem., 1998, 70, 647R-716R; Biemann, Ann. Rev. Biochem., 1992, 61, 977-1010; and Crain et al., Curr. Opin. Biotechnol., 1998, 9, 25-34). While interactions that lead to covalent modification of biopolymers have been studied for some time, one of the most significant developments in the field has been the observation, under appropriate solution conditions and analyte concentrations, of specific non-covalently associated macromolecular complexes that have been promoted into the gas-phase intact (Loo, Mass Spectrometry Reviews, 1997, 16, 1-23; Smith et al., Chemical Society Reviews, 1997, 26, 191-202; Ens et al., Standing and Chernushevich, Eds., New Methods for the Study of Biomolecular Complexes, Proceedings of the NATO Advanced Research Workshop, held 16-20 Jun. 1996, in Alberta, Canada, in NATO ASI Ser., Ser. C, 1998, 510, Kluwer, Dordrecht, Netherlands).

A variety of non-covalent complexes of biomolecules have been studied using ESI-MS and reported in the literature (Loo, Bioconjugate Chemistry, 1995, 6, 644-665; Smith et al., J. Biol. Mass Spectrom. 1993, 22, 493-501; Li et al., J. Am. Chem. Soc., 1993, 115, 8409-8413). These include the peptide-protein complexes (Busman et al., Rapid Commun. Mass Spectrom., 1994, 8, 211-216; Loo et al., Biol. Mass Spectrom., 1994, 23, 6-12; Anderegg and Wagner, J. Am. Chem. Soc., 1995, 117, 1374-1377; Baczynskyj et al., Rapid Commun. Mass Spectrom., 1994, 8, 280-286), interactions of polypeptides and metals (Loo et al., J. Am. Soc. Mass Spectrom., 1994, 5, 959-965; Hu and Loo, J. Mass Spectrom., 1995, 30, 1076-1079; Witkowska et al., J. Am. Chem. Soc., 1995, 117, 3319-3324; Lane et al., J. Cell Biol., 1994, 125, 929-943), and protein-small molecule complexes (Ganem and Henion, ChemTracts-Org. Chem., 1993, 6, 1-22; Henion et al., Ther. Drug Monit., 1993, 15, 563-569; Ganguly et al., Tetrahedron, 1993, 49, 7985-7996, Baca and Kent, J. Am. Chem. Soc., 1992, 114, 3992-3993). Further, the study of the quaternary structure of multimeric proteins (Baca and Kent, J. Am. Chem. Soc., 1992, 114, 3992-3993; Light-Wahl et al., J. Am. Chem. Soc., 1994, 116, 5271-5278; Loo, J. Mass Spectrom., 1995, 30, 180-183, Fitzgerald et al., Proc. Natl. Acad. Sci. USA, 1996, 93, 6851-6856), and of nucleic acid complexes (Light-Wahl et al., J. Am. Chem. Soc., 1993, 115, 803-804; Gale et al., J. Am. Chem. Soc., 1994, 116, 6027-6028; Goodlett et al., Biol. Mass Spectrom., 1993, 22, 181-183; Ganem et al., Tet. Lett., 1993, 34, 1445-1448; Doctycz et al., Anal. Chem., 1994, 66, 3416-3422; Bayer et al., Anal. Chem., 1994, 66, 3858-3863; Greig et al., J. Am. Chem. Soc., 1995, 117, 10765-766), protein-DNA complexes (Cheng et al., Proc. Natl. Acad. Sci. U.S.A., 1996, 93, 7022-7027), multimeric DNA complexes (Griffey et al., Proc. SPIE-Int. Soc. Opt. Eng., 1997, 2985, 82-86), and DNA-drug complexes (Gale et al., JACS, 1994, 116, 6027-6028) are known in the literature.

ESI-MS has also been effectively used for the determination of binding constants of non-covalent macromolecular complexes such as those between proteins and ligands, enzymes and inhibitors, and proteins and nucleic acids. The use of ESI-MS to determine the dissociation constants ($K_D$)

for oligonucleotide-bovine serum albumin (BSA) complexes have been reported (Greig et al., J. Am. Chem. Soc., 1995, 117, 10765-10766). The $K_D$ values determined by ESI-MS were reported to match solution $K_D$ values obtained using capillary electrophoresis.

ESI-MS measurements of enzyme-ligand mixtures under competitive binding conditions in solution afforded gas-phase ion abundances that correlated with measured solution-phase dissociation constants ($K_D$) (Cheng et al., JACS, 1995, 117, 8859-8860). The binding affinities of a 256-member library of modified benzenesulfonamide inhibitors to carbonic anhydrase were ranked. The levels of free and bound ligands and substrates were quantified directly from their relative abundances as measured by ESI-MS and these measurements were used to quantitatively determine molecular dissociation constants that agree with solution measurements. The relative ion abundance of non-covalent complexes formed between D- and L-tripeptides and vancomycin group antibiotics were also used to measure solution binding constants (Jorgensen et al., Anal. Chem., 1998, 70, 4427-4432).

ESI techniques have found application for the rapid and straightforward determination of the molecular weight of certain biomolecules (Feng and Konishi, Anal. Chem., 1992, 64, 2090-2095; Nelson et al., Rapid Commun. Mass Spectrom., 1994, 8, 627-631). These techniques have been used to confirm the identity and integrity of certain biomolecules such as peptides, proteins, oligonucleotides, nucleic acids, glycoproteins, oligosaccharides and carbohydrates. Further, these MS techniques have found biochemical applications in the detection and identification of post-translational modifications on proteins. Verification of DNA and RNA sequences that are less than 100 bases in length has also been accomplished using ESI with FTMS to measure the molecular weight of the nucleic acids (Little et al, Proc. Natl. Acad. Sci. USA, 1995, 92, 2318-2322).

While data generated and conclusions reached from ESI-MS studies for weak non-covalent interactions generally reflect, to some extent, the nature of the interaction found in the solution-phase, it has been pointed out in the literature that control experiments are necessary to rule out the possibility of ubiquitous non-specific interactions (Smith and Light-Wahl, Biol. Mass Spectrom., 1993, 22, 493-501). The use of ESI-MS has been applied to study multimeric proteins because the gentleness of the electrospray/desorption process allows weakly-bound complexes, held together by hydrogen bonding, hydrophobic and/or ionic interactions, to remain intact upon transfer to the gas phase. The literature shows that not only do ESI-MS data from gas-phase studies reflect the non-covalent interactions found in solution, but that the strength of such interactions may also be determined. The binding constants for the interaction of various peptide inhibitors to src SH2 domain protein, as determined by ESI-MS, were found to be consistent with their measured solution phase binding constants (Loo et al., Proc. 43$^{rd}$ ASMS Conf. on Mass Spectrom. and Allied Topics, 1995). ESI-MS has also been used to generate Scatchard plots for measuring the binding constants of vancomycin antibiotics with tripeptide ligands (Lim et al., J. Mass Spectrom., 1995, 30, 708-714).

Similar experiments have been performed to study non-covalent interactions of nucleic acids. ESI-MS has been applied to study the non-covalent interactions of nucleic acids and proteins. Stoichiometry of interaction and the sites of interaction have been ascertained for nucleic acid-protein interactions (Jensen et al., Rapid Commun. Mass Spectrom., 1993, 7, 496-501; Jensen et al., 42$^{nd}$ ASMS Conf. on Mass Spectrom. and Allied Topics, 1994, 923). The sites of interaction are typically determined by proteolysis of either the non-covalent or covalently crosslinked complex (Jensen et al., Rapid Commun. Mass Spectrom., 1993, 7, 496-501; Jensen et al., 42$^{nd}$ ASMS Conf. on Mass Spectrom. and Allied Topics, 1994, 923; Cohen et al., Protein Sci., 1995, 4, 1088-1099). Comparison of the mass spectra with those generated from proteolysis of the protein alone provides information about cleavage site accessibility or protection in the nucleic acid-protein complex and, therefore, information about the portions of these biopolymers that interact in the complex.

Fourier transform ion cyclotron resonance mass spectrometry (FT-ICR MS) is an especially useful analytical technique because of its ability to resolve very small mass differences to make mass measurements with a combination of accuracy and resolution that is superior to other MS detection techniques, in connection with ESI ionization (Amster, J. Mass Spectrom., 1996, 31, 1325-1337, Marshall et al., Mass Spectrom. Rev., 1998, 17, 1-35). FT-ICR MS may be used to obtain high resolution mass spectra of ions generated by any of the other ionization techniques. The basis for FT-ICR MS is ion cyclotron motion, which is the result of the interaction of an ion with a unidirectional magnetic field. The mass-to-charge ratio of an ion (m/q or m/z) is determined by a FT-ICR MS instrument by measuring the cyclotron frequency of the ion.

The insensitivity of the cyclotron frequency to the kinetic energy of an ion is one of the fundamental reasons for the very high resolution achievable with FT-ICR MS. Each small molecule with a unique elemental composition carries an intrinsic mass label corresponding to its exact molecular mass, identifying closely related library members bound to a macromolecular target requires only a measurement of exact molecular mass. The target and potential ligands do not require radio labeling, fluorescent tagging, or deconvolution via single compound re-synthesis. Furthermore, adjustment of the concentration of ligand and target allows ESI-MS assays to be run in a parallel format under competitive or non-competitive binding conditions. Signals can be detected from complexes with dissociation constants ranging from <10 nM to ~100 mM. FT-ICR MS is an excellent detector in conventional or tandem mass spectrometry, for the analysis of ions generated by a variety of different ionization methods including ESI, or product ions resulting from collisionally activated dissociation.

FT-ICR MS, like ion trap and quadrupole mass analyzers, allows selection of an ion that may actually be a weak non-covalent complex of a large biomolecule with another molecule (Marshall and Grosshans, Anal. Chem., 1991, 63, A215-A229; Beu et al., J. Am. Soc. Mass Spectrom., 1993, 4, 566-577; Winger et al., J. Am. Soc. Mass Spectrom., 1993, 4, 566-577; Huang and Henion, Anal. Chem., 1991, 63, 732-739), or hyphenated techniques such as LC-MS (Bruins et al., Anal. Chem., 1987, 59, 2642-2646; Huang and Henion, J. Am. Soc. Mass Spectrom., 1990, 1, 158-65; Huang and Henion, Anal. Chem., 1991, 63, 732-739) and CE-MS experiments (Cai and Henion, J. Chromatogr., 1995, 703, 667-692). FTICR-MS has also been applied to the study of ion-molecule reaction pathways and kinetics.

The use of ESI-FT-ICR mass spectrometry as a method to determine the structure and relative binding constants for a mixture of competitive inhibitors of the enzyme carbonic anhydrase has been reported (Cheng et al., J. Am. Chem. Soc., 1995, 117, 8859-8860). Using a single ESI-FT-ICR MS experiment these researchers were able to ascertain the relative binding constants for the noncovalent interactions between inhibitors and the enzyme by measuring the relative abundances of the ions of these noncovalent complexes. Further, the $K_D$s so determined for these compounds paralleled their known binding constants in solution. The method was also capable of identifying the structures of tight binding ligands from small mixtures of inhibitors based on the high-resolution capabilities and multistep dissociation mass spectrometry afforded by the FT-ICR technique. A related study (Gao et al., J. Med. Chem., 1996, 39, 1949-55) reports the use of ESI-FT-ICR MS to screen libraries of soluble peptides in a search for tight binding inhibitors of carbonic anhydrase II. Simultaneous identification of the structure of a tight binding peptide inhibitor and determination of its binding constant was performed. The binding affinities determined from mass spectral ion abundance were found to correlate well with those determined in solution experiments. Heretofore, the applicability of this technique to drug discovery efforts is limited by the lack of information generated with regards to sites and mode of such non-covalent interactions between a protein and ligands.

Electrospray ionization (ESI) has found wide acceptance in the field of analytical mass spectrometry since it is a gentle ionization method which produces multiply charged ions from large molecules with little or no fragmentation and promotes them into the gas phase for direct analysis by mass spectrometry. ESI sources operate in a continuous mode with flow rates ranging from <25 mL/min to 1000 µL/min. The continuous nature of the ion source is well suited for mass spectrometers which employ the m/z scanning, such as quadrupole and sector instruments, as their coupling constitutes a continuous ion source feeding in a nearly continuous mass analyzer. As used in this invention the electrospray ionization source may have any of the standard configurations including but not limited to Z-spray, microspray, off-axis spray or pneumatically assisted electrospray. All of these can be used in conjunction with or without additional countercurrent drying gas. Further the mass spectrometer can include a gated ion storage device for effecting thermolysis of test mixtures.

When the solvated ions generated from electrospray ionization conditions are introduced into the mass spectrometer, the ions are subsequently desolvated in an evaporation chamber and are collected in a rf multi-pole ion reservoir (ion reservoir). A gas pressure around the ion reservoir is reduced to $10^{-3}$-$10^{-6}$ torr by vacuum pumping. The ion reservoir is preferably driven at a frequency that captures the ions of interest and the ensemble of ions are then transported into the mass analyzer by removing or reversing the electric field generated by gate electrodes on either side of the ion reservoir. Mass analysis of the reacted or dissociated ions are then performed. Any type of mass analyzers can be used in effecting the methods and process of the invention. These include, but are not limited to, quadrupole, quadrupole ion trap, linear quadrupole, time-of-flight, FT-ICR and hybrid mass analyzers. A preferred mass analyzer is a FT-ICR mass analyzer.

Seen in FIG. 1 is a schematic representation of a mass spectrometer. A review of the mass spectrometer will facilitate understanding of the invention as it includes various component parts that may be included in one or more of the various types of different mass spectrometers. The spectrometer 10 includes a vacuum chamber 12 that is segmented into a first chamber 14 and a second chamber 16. The mass spectrometer 10 is shown as an electrospray mass spectrometer. A metallic micro-electrospray emitter capillary 18 having an electrode 20 is positioned adjacent to the vacuum chamber 12. The electrode/metallic capillary serves as an ion emitter. The capillary 18 is positioned on an X-Y manipulator for movement in two planes.

Adjacent to the capillary 18 and extending from the vacuum chamber 16 is an evaporative chamber 22 having a further capillary 24 extending axially along its length. The X-Y manipulator allows for precise positioning of the capillary 18 with respect to the capillary 24. A plume of ions carried in a solvent is emitted from the emitter capillary 18 towards the evaporator capillary 24. The evaporator capillary 24 serves as an inlet to the interior of vacuum chamber 12 for that portion of the plume directly in line with the evaporator capillary 24.

Within the first chamber 14 is a skimmer cone 26. This skimmer cone 26 serves as a lens element. In line with the skimmer cone 26 is an ion reservoir 28. A port 30 having a valve is connected to a conventional first vacuum source (not shown) for reducing the atmospheric pressure in the first chamber 14 to create a vacuum in that chamber. Separating chambers 14 and 16 is a gate electrode 32.

The ion reservoir 28 can be one of various reservoirs such as a hexapole reservoir. Ions, carried in a solvent, are introduced into chamber 14 via the evaporator capillary 24. Solvent is evaporated from the ions within the interior of capillary 24 of the evaporator chamber 22. Ions travel through skimmer cone 26 towards the electrode 32. By virtue of their charge and a charge placed on the electrode 32 the ions can be held in the reservoir.

The electrode 32 includes an opening. Ions are released from the ion reservoir 28 by modifying the potential on the electrode 32. They then can pass through the opening into the second vacuum chamber 16 towards a mass analyzer 34. For use in FT-ICR, positioned with respect to the analyzer 34 is a magnet (not shown). The second vacuum chamber 16 includes port 36 having a valve. As with valve 30 in chamber 14, this valve 36 is attached to an appropriate vacuum pump for creating a vacuum in chamber 16. Chamber 16 may further include a window or lens that is positioned in line with a laser. The laser can be used to excite ions in either the mass analyzer 34 or the ion reservoir.

In effecting the methods and processes of the invention, a set of compounds are probed against a target molecule, using the mass spectrometer, to identify those compounds, i.e., ligands, from the set of compounds that are "weak" binders with respect to the target molecule. For the purposes of this invention "weak" binding is defined as binding in the millimolar (mM) range. Typically ligands will have a binding affinity in the range of 0.2 to 10 nM. As opposed to other techniques, the mass spectrometer will not fail to detect these weak mM interactions. Ligands having preferred binding characteristics with respect to a target molecule are selected. After selection, the binding mode of the ligands is determined by re-screening mixtures of ligands against the target molecule. Re-screening is effected by simultaneously exposing the target molecule against a small set of two more ligands. As a result of this screening, ligands that can not bind at overlapping sites, competitive binding, are differentiated from those that can bind at remote sites simultaneously, concurrent binding, and those that can bind in a way that traps one compound, cooperative binding as well as those having "mixed" binding modes.

Ligands having selected binding characteristics are identified and their structure activity relationship (SAR) with respect to target binding is probed using the mass spectrometer. Two or more ligands can be joined by concatenation into new structural configurations to create a new ligand that will have improved binding characteristics or properties. Thus starting from small, rigid ligands that bind with weak affinity, more complex molecules that bind to specific target molecules with high affinity can be identified using mass spectrometry. This is effected using the mass spectrometer as the primary tool and does not involve extensive chemical synthesis or extensive molecular modeling.

Concatenation can be effected based on empirical or computational predictions. Thus concatenation will yield either new synthetic chemical ligands having new properties or in silico virtual ligands. In conjunction with molecular modeling tools, the virtual ligands can be used to identify probable binding locations on the target molecule.

In concatenating ligands together using the methods and processes of the invention, two ligands that have mM (millimolar) affinities might be joined and yield a concatenated ligand that might have nM affinity (nanomolar). While we do not wish to be bound by theory, we presently believe this result has multiple contributing factors. There can be a gain in intrinsic binding energy, i.e., loss of translational entropy, when both fragments always bind at the same time. Proper geometry for both fragments can result in a favorable enthalpy of interaction, i.e., no loss of binding enthalpy. Fewer degrees of freedom resulting from two fragments being linked through bonds with limited rotation will result in a loss of rotational entropy that equals a gain in binding energy. And there can be some energy gain (enthalpy and entropy) from desolvation of the target and the ligand fragments. The net result can be a $10^3$ to a $10^6$ improvement in binding affinity, i.e., a 4-6 kcal/mol gain in binding energy.

Newly synthesized concatenated ligand molecules, which retain the best conformations and locations of the ligand fragments with respect to the target, can be re-probed using the mass spectrometer to ascertain the binding characteristics of the new molecule. Repeated iteration of the process and methods of the invention can improve the binding affinity of these new molecules. The newly synthesized concatenated ligand molecules can also be screened using a functional assay that involves the target.

The target molecule can be any target of interest. Preferred as targets are molecules of biological interest especially RNA, proteins, RNA-DNA duplexes, DNA duplexes, polysaccharides, phospholipids and glycolipids. A particularly preferred target molecule is RNA. As practiced herein, the target molecule can, itself, be a fragment of a larger molecule, as for instance, RNA that is a fragment of a larger RNA. Particularly preferred as a target molecule is RNA especially RNA that is a fragment of a larger RNA. A further preferred target molecule is double stranded DNA targeted with ligands that are transcription factors.

The initial weak binding ligands can be selected from various sources including, but not limited to, collection libraries of diverse compounds. These include, but are not limited to, historical repositories of compounds, collections of natural products, collections of drug substances, collections of intermediates produced in forming drug substances, collections of dye stuffs, commercial collections of chemical substances or combinatorial libraries of related compounds. Many universities and pharmaceutical companies maintain historical repositories of all compounds synthesized. These can include drugs substances that have or have not been screened for biological activity, intermediates used in the preparation of such drug substances and derivatives of such drug substances. A typical pharmaceutical company might have millions of such repository samples. Other collections of compounds include collections of natural occurring compounds or derivatives of such natural occurring compounds. Irrespective of the origin of the compounds, the compound collections can be categorized by size, structure, function or other various parameters.

Commercial chemical supply houses also have collections of compounds that are suitable for screening against target molecules. Again these might be categorized by various parameter that can be useful in selecting sets of compounds for screening against a target molecule to identify weak binding ligands for that target molecule. Other ligand molecule candidates might be specifically synthesized to include one or more features. One preferred method to assemble a group of compounds useful for selecting binding ligands is by effecting a combinatorial synthesis of a group of related compounds using various methods that are available in the art of combinatorial chemistry. Irrespective of the source of the ligands, i.e., from a collection or specifically synthesized according to define criteria, the ligands will contain various motifs, i.e., stacking, electrostatic and H-bonding, that contribute to the weak binding of the ligands with the target.

The collections of compound for consideration as ligands for target molecules, typically categorized by size, structure or function, can be assembled as a library or set of compounds having from 2 to about 100,000 or less members. In a first preferred group of compounds selected for consideration as ligands for a target molecule each member of the group would be selected to independently have a molecular mass less than about 1000 Daltons and fewer than 15 rotatable bonds. In a more preferred group of compounds, each member of the group will be selected to independently have a molecular mass less than about 600 Daltons and fewer than 8 rotatable bonds. In a more preferred group of compounds each of member of the group will be selected to independently have a molecular mass less than about 200 Daltons, have fewer than 4 rotatable bonds or no more than one sulfur, phosphorous or halogen atom. A particularly useful solvent for use in screening potential ligands for an RNA target is dimethylsulfoxide. In a particularly preferred method of the invention, the potential ligands are selected as compounds having at least 20 mM solubility in dimethylsulfoxide.

In screening a compound set for potential binding ligands, sample preparation and certain basic operations of the mass spectrometer are optimized to preserve the weak non-covalent complexes formed between ligands and the target molecule. These include extra care in desalting the target molecule as well as a general reduction of the temperature of the desolvation capillary compared to the temperature that would be used if the only interest was in analyzing the target molecule itself. Also the voltage potential across the capillary exit and the first skimmer cone, i.e., lens element, is optimized to ensure good desolvation. A further consideration is selection of the buffer concentration and solvent to insure good solvation.

Detection of weak non-covalent complexes using ESI-MS is a function of both instrument parameters and solution conditions. In solution, high concentrations of buffer can be used to reduce formation of non-specific electrostatic or hydrogen-bonded aggregates. The observation of weak complexes depends on the level of collisional activation that occurs along the path from the atmospheric region to the high vacuum region. Variables that impact the degree of collisional activation include the flow rate and temperature of countercurrent drying gas, desolvation capillary temperature, ESI needle position, capillary-skimmer potential difference, droplet size, and pressure in the region of the supersonic expansion beyond the desolvation capillary. Preferably, these variables are iteratively adjusted on any ESI-MS instrument to optimize the detection of weak non-covalent complexes.

A number of parameters influence the "harshness" of the ESI source, including the rate of drying produced by countercurrent gas and the temperature of the desolvation capillary, the gas pressure in the region of supersonic expansion beyond the desolvation capillary, and the effective electric field generated by the potential difference between the desolvation capillary and the first skimmer cone. For example, it has been observed that desolvated ions can be formed from partially desolvated droplets that traverse a low temperature desolvation capillary when the voltage difference between the capillary and the skimmer cone is increased on the LCQ mass spectrometer. Although the improved performance with increased energy would seem to be counterintuitive, the viscous drag of ions following supersonic expansion from the capillary provides a mild method for removal of residual waters of hydration without disruption of complexes (such as ammonium) stabilized by a single hydrogen bond.

It is possible to measure the relative gas-phase binding energies of ligands through CAD of the ternary complexes, individually or in parallel. This information can be used to establish the order and proximity of binding when a ligand with higher binding energy is preferentially dissociated from the complex. For example, the hydroxyl groups of glucosamine (GA) may not compete effectively with waters of hydration for binding to target 16S ribosomal RNA in solution. However, in the gas phase, these hydroxyls can bind to the desolvated RNA and enhance the apparent stability of the complex.

In selecting potential weak binding ligands for a target molecule a standard ligand is used as a reference ligand for that target. Various standard ligands will be used for different targets. In one sense, these standard ligands can be thought of as ion thermometers. With any target molecule, the standard compounds will typically be selected such that its has a binding affinity, as measured as a dissociation constant, i.e., Kd, of the order of nanomolar to about 100 millimolar for its target molecule. A more preferred range would be from 10 to 50 mM with 50 mM binding affinity for the target molecule being the most preferred.

For use with RNA or DNA targets we have found ammonium (from acetate, chloride, borate or other salts), primary amines (including by not limited to alkyl amines such as methylamine and ethylamine), secondary amines (including but not limited to dialkylamines such as dimethylamine and diethylamine), tertiary amines (including by not limited to trialkyl amines such as triethylamine, trimethylamine and dimethylethyl amine), amino acids (including but not limited to glycine, alanine, tryptophan and serine) and nitrogen containing heterocycles (including but not limited to imidazole, triazole, triazine, pyrimidine and pyridine) are particularly useful. These standard ligands will typically have a binding affinity, as measured as a dissociation constant, i.e., Kd, of the order of nanomolar to about 100 millimolar for the RNA or DNA target. Ammonium is particularly useful for RNA since it has a binding affinity for RNA, as measure by its dissociation constant, i.e., Kd, of about 50 mM.

Other standard ligands will be used for other target molecules. For use with protein target molecules, esters such as formate, acetate and propionate, phosphates, borates, amino acids and nitrogen containing heterocycles (including but not limited to imidazole, triazole, triazine, pyrimidine and pyridine) are particularly useful. As with the above described RNA and DNA target molecules, for protein target molecules as well as for other target molecules, the standard ligands will typically have a binding affinity, as measured as a dissociation constant, i.e., Kd, of the order of nanomolar to about 100 millimolar for the target.

By selecting the binding affinity for the standard ligand as described, the operating performance conditions of the mass spectrometer are adjusted such that the signal strength of the standard ligand to that of the target molecule of from 1% to about 30% of the signal strength of unbound target. One or more of the candidate ligands from a set of compounds is next screened with a mixture of the target molecule and the standard ligand. Those candidate ligands having weak affinities can be identified by the presence of a signal that is greater than the background noise of the mass spectrometer. By adjustment of the operating conditions of the mass spectrometer using the standard ligands, non-binding ligands are not detected by the mass spectrometer.

The candidate ligands can be screened one at a time or in sets. A typical set would have from 2 to 10 members. A more preferred set has from 4 to 8 members. The compound set is screened for members that form non-covalent complexes with the target molecule using the mass spectrometer. The relative abundances and stoichiometries of the non-covalent complexes with the target molecule are measured from the integrated ion intensities. These results can be stored in a relational database that is cross-indexed to the structure of the compounds.

For a typical RNA target, the RNA is selected as an RNA molecule have from about 10 to about 200 nucleotides. This RNA can be an isolated or purified fragment of a larger RNA or it can be a synthetic RNA. Such synthetic RNA can be a mimic of a natural RNA. A more preferred RNA target molecule would have from about 15 to about 100 nucleotides. The RNA can have both secondary and ternary structure.

Having derived a set of ligands that bind to the target molecule, in one embodiment of the invention, simple derivative of these ligands are made by modifying the ligand. These modifications include modification by addition of methyl, amino, nitro, hydroxyl, bromo, thio groups or other small substituent group or derivatives where the composition and size of rings and side chains have been varied. These derivatives can then be screened as above to obtain SAR information and to optimize the binding affinity with the target.

Depending on the size of the compound collection used above, from 2 to 10,000 compounds may form complexes with the target. These compounds are pooled into groups of 4-10 and screened again as a mixture against the target as before. Since all of the compounds have been shown previously to bind to the target, three possible changes in the relative ion abundances are observed in the mass spectrometry assay. If two compounds bind at the same site, the ion abundance of the target complex for the weaker binder will be decreased through competition for target binding with the higher affinity binder (competitive binding). If two compounds can bind at distinct sites, signals will be observed from the respective binary complexes with the target and from a ternary complex where both compounds bind to the target simultaneously (concurrent binders). If the binding of one compound enhances the binding of a second compound, the ion abundance from the ternary complex will be enhanced relative to the ion abundances from the respective binary complexes (cooperative binding). If the ratio of the relative ion abundances is greater than 1, the binding is considered to be cooperative. These ratios of relative ion abundances are calculated and can be stored in a database for all compounds that bind to the target.

Compounds that bind concurrently are further analyzed. Derivatives of concurrent binders can be prepared with addition of an added moiety, including but not limited to methyl, ethyl, isopropyl, amino, methylamino, dimethylamino, trifluoromethyl, methoxy, thiomethyl or phenyl at different positions around the original compound that binds. These derivatives can be re-screened as a mixture with compounds that bound concurrently to the starting compound. If the additional methyl, ethyl, isopropyl, or phenyl moiety occupies space that the concurrent binder occupied, the two compounds will bind competitively. Observation of this change in the mode of binding using the mass spectrometer indicates the two molecules are spatially proximate as a result of the chemical modification. Correlation of the change in binding mode with the size and position of the chemical modification can be used as a "molecular ruler" to measure the distance between two compounds on the surface of the RNA. Compounds that bind in a cooperative or competitive mode do so by binding in close proximity on the target surface. Locations where addition of a moiety has no effect on the binding mode are potential sites of covalent attachment between the two molecules. This information can be used in conjunction with molecular modeling of the target-ligand complex to generate a pharmacophore map of the chemical groups that bind to the target surface.

In some cases, a 3-dimensional working model of the target structure may be available based on NMR or chemical and enzymatic probing data. These 3-D models of the target can be used with computational programs such as MCSS (MSI, San Diego) or QXP (Thistlesoft, Groton, Conn.) to locate the possible sites of binding with the ligand. MCSS, QCP and similar programs perform a Monte Carlo-based search for sites where the ligand can bind, and rank order the sites based on a scoring scheme. The scoring scheme calculates hydrophobic, hydrogen-bonding, and electrostatic interactions between the ligand and target. The small molecules may bind at many locations along the surface of the target. However, there are some locations that are preferred. These calculations can be performed for molecules that bind competitively or cooperatively, and favorable binding conformations whose proximity is based on the "molecular ruler" as described above can be identified.

In one embodiment of the invention, the QXP program is used to search all interaction space around a RNA target molecule and to cluster the results. From the clustered results the highest probability, low-energy binding sites for binding ligands is identified. All the interaction space around the RNA target is searched for proximate binding sites between ligands. The distances between the ligands are measured to obtain the lengths of linkers required to connect functional group sites on the ligands for best scaffold binding. The search also is used to insure that the lowest energy conformation retains the best binding contacts.

In conjunction with the developers of QXP, the UNIX version of the QXP program designed to run on a SGI computer having 128 processors was ported to a LINUX version that runs on a PC platform having 56 processors. This resulted in an advantage in maximizing the price to performance ratio of the hardware. The computationally intensive nature of identifying global energy minimum for a combinatorial library of small molecule, typically with 8-12 rotatable bonds, bound to the receptor is particularly well suited to the "distributed computing" method. The compound library is divided into the number of available computational resources and thus the docking calculations are run in "parallel". This method exploits the available CPU cycles over a cluster of extremely fast PC boxes networked together in a system commonly referred to as a Beowulf-class cluster. Beowulf-class clusters are described by E. Wilson in Chemical & Engineering News (2000, 78(2):27-31) The PC platform used included 16 PCs, dual Intel pentium II 450 MHz processors, 256 MB RAM and 6.4 GB disk and 12 PCs, dual Intel pentium II 400 MHz processors, 256 MB RAM and 6.4 GB disk totaling 56 processors. A benchmark calculation using 350 MHz Pentium II processors indicated, in terms of speed, that PC boxes clustered together as described would outperform a R5000SGI O2 machine.

The same result is reported to be accomplished using the MCSS software, i.e., MCSS/HOOK. As reported by its manufacture, MSI, San Diego, Calif., for proteins, MCSS/HOOK characterizes an active site's ability to bind ligands using energetics calculated via CHARMm. Strongly bound ligands are linked together automatically to provide de novo suggestions for drug candidates. The software is reported to provide a systematic, comprehensive approach to ligand development and de novo ligand design that result in synthetically feasible molecules. Using libraries of functional groups and molecules, MCSS is reported to systematically searches for energetically feasible binding sites in a protein. HOOK is reported to then systematically searches a database for skeletons which logically might connect these binding sites in the presence of the protein. HOOK attempts to link multiple functional groups with molecular templates taken from the its database. The results are potential compounds that are consistent with the geometry and chemistry of the binding site.

An embodiment of the invention relates to methods of determining the relative interaction of ligands that bind to a target substrate. The exposure of a target substrate to a mixture of two or more ligands allows for the formation of non-covalent complexes. Analysis of the mixture by mass spectrometry enables the identification of the complexes formed, the relative affinities of the ligands and ultimately the type of interaction between the ligands for the target. In the simplest situation, two ligands known to bind to a target are mixed together and screened by mass spectrometry leading to three conditional relationships; competitive, concurrent and cooperative binding.

Competitive Binding

Ligands bind competitively for a target when the binding of one ligand prevents the binding of the other ligand is the result of the ligands binding to the target at the same location. In this situation, the mixture contains an equilibrium of two binary complexes, one of which being one ligand bound to the target and the other being the other ligand bound to the target. The ligand having the greater affinity for the target will predominate and thus have higher signal intensity for its binary complex with the target compared to the other ligand. Competitive binding interaction between two ligands is determined according to methods of the invention by analyzing the mixture by mass-spectrometry to detect the presence or lack of signal corresponding to a ternary complex where both ligands are bound to the target at the same time. The lack of signal for a ternary complex indicates a competitive binding interaction between the two ligands while the presence of the signal indicates a non-competitive interaction.

Accordingly, in an aspect of the present invention, there is provided a method for determining the relative interaction between at least two ligands with respect to a target substrate. In practicing this method an amount of each of the ligands is mixed with an amount of the target substrate to form a mixture. This mixture is analyzed by mass spectrometry to determine the presence or absence of a ternary complex corresponding to the simultaneous adduction of two of the ligands with the target substrate. The absence of the ternary complex indicates that binding of the ligands to the target substrate is competitive and the presence of the ternary complex indicates that binding of the ligands to the target substrate is other than competitive.

Figure 3:
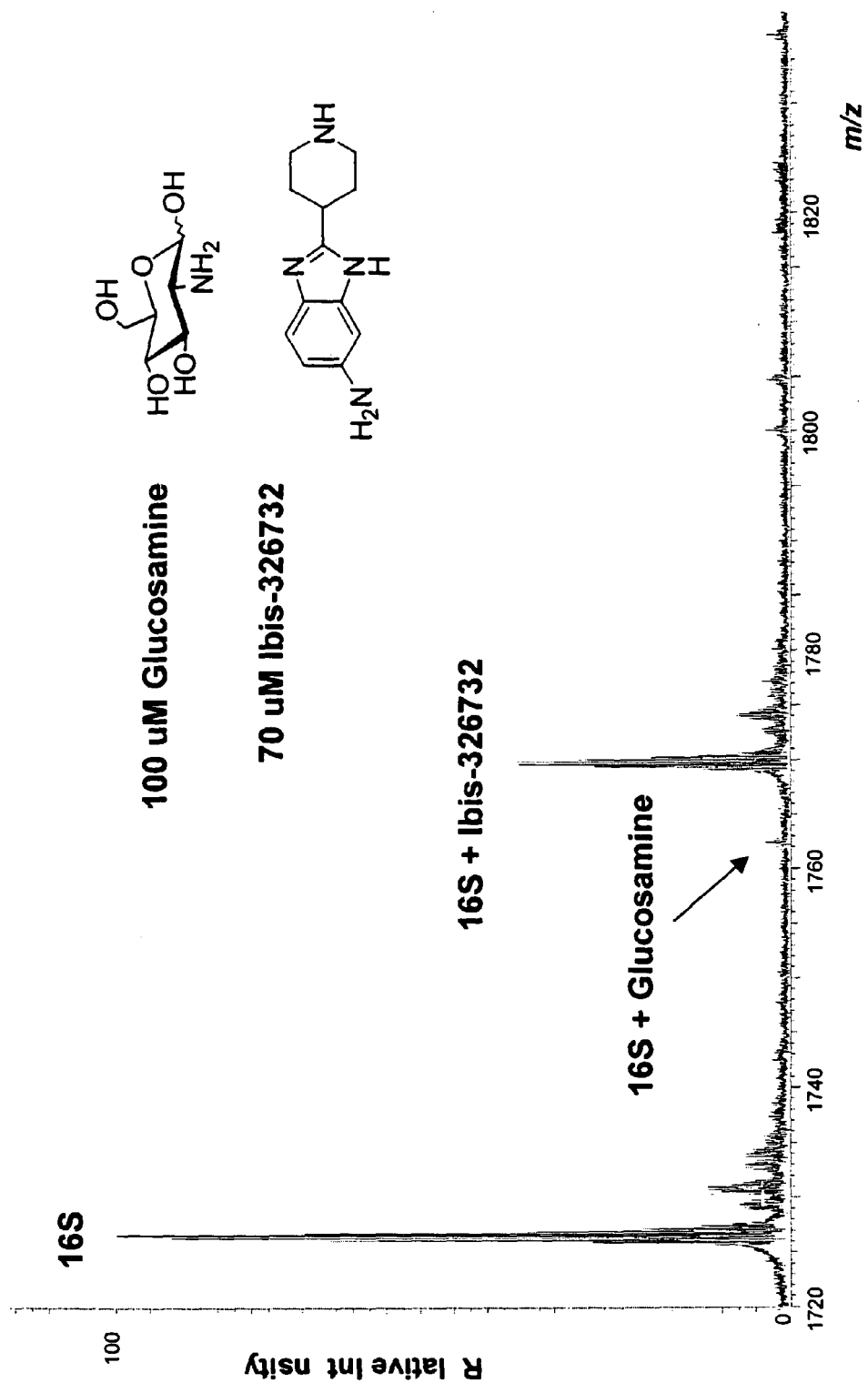
FIG. 3 is a mass spectrum showing competitive displacement of glucosamine from the 16S RNA fragment by Ibis-326732.

The above method for determining a competitive binding interaction of two ligands is exemplified in FIG. 3 wherein 70 µM of a small molecule Ibis-326732 (4-amino-2-piperidin-4-ylbenzimidazole) was added to a solution of 100 µM glucosamine and 5 µM of a 27 nucleotide fragment of bacterial 16S ribosomal RNA incorporating the A-site. The mass-spectrum trace for the mixture lacks an intensity signal for a ternary complex of the two ligands Ibis-326732 and glucosamine simultaneously bound to the target 16S RNA. This indicates that the two ligands are competitive binders for this target i.e. bind to the same site. Further, a comparison of the ion abundance of the two binary complexes at approximately 1762 and 1770 m/z indicates that Ibis-326732 binds to the target RNA with greater affinity than glucosamine.

Concurrent Binding

Ligands bind concurrently when the binding of one ligand to the target is unaffected by the binding of the other and is a consequence of the ligands binding to the target at distinct sites. In this situation, a mixture containing two concurrent binding ligands will have an equilibrium of two binary complexes, one being first ligand bound to the target and the other being the second ligand bound to the target as well as a ternary complex of both ligands bound to the target and unbound target substrate. The ligand having the greater affinity for the target will have higher signal intensity for its binary complex with the target compared to the other ligand. Concurrent binding interaction between two ligands is determined according to methods of the invention by analyzing the mixture by mass-spectrometry and comparing the ratios of the ion abundance of the complexes. Particularly, the absolute ion abundance of the ternary complex (TL1L2) is compared to the relative ion abundance of the binary complexes (TL1 and TL2) which contribute to the formation of the ternary complex with respect to the unbound target (TL1×TL2/T). Since there are two binary complexes contributing the formation of the ternary complex, the comparison is with the sum of the two contributing binary complexes i.e. TL1×TL2/T+TL2×TL1/T. If the absolute ion abundance of the ternary complex is equal to the sum of the relative ion abundance of the contributing binary complexes, then the two ligands concurrently bind to the target substrate. Expressed another way, a pair of ligands are concurrent binders for a target if in either of the following equivalent formulae the value of y is equal to zero:

$$y = TL1L2 - TL1 \times \frac{TL2}{T} - TL2 \times \frac{TL1}{T}$$

or $$y = \frac{TL1L2}{T} - 2 \times TL1 \times TL2$$

Figure 4:
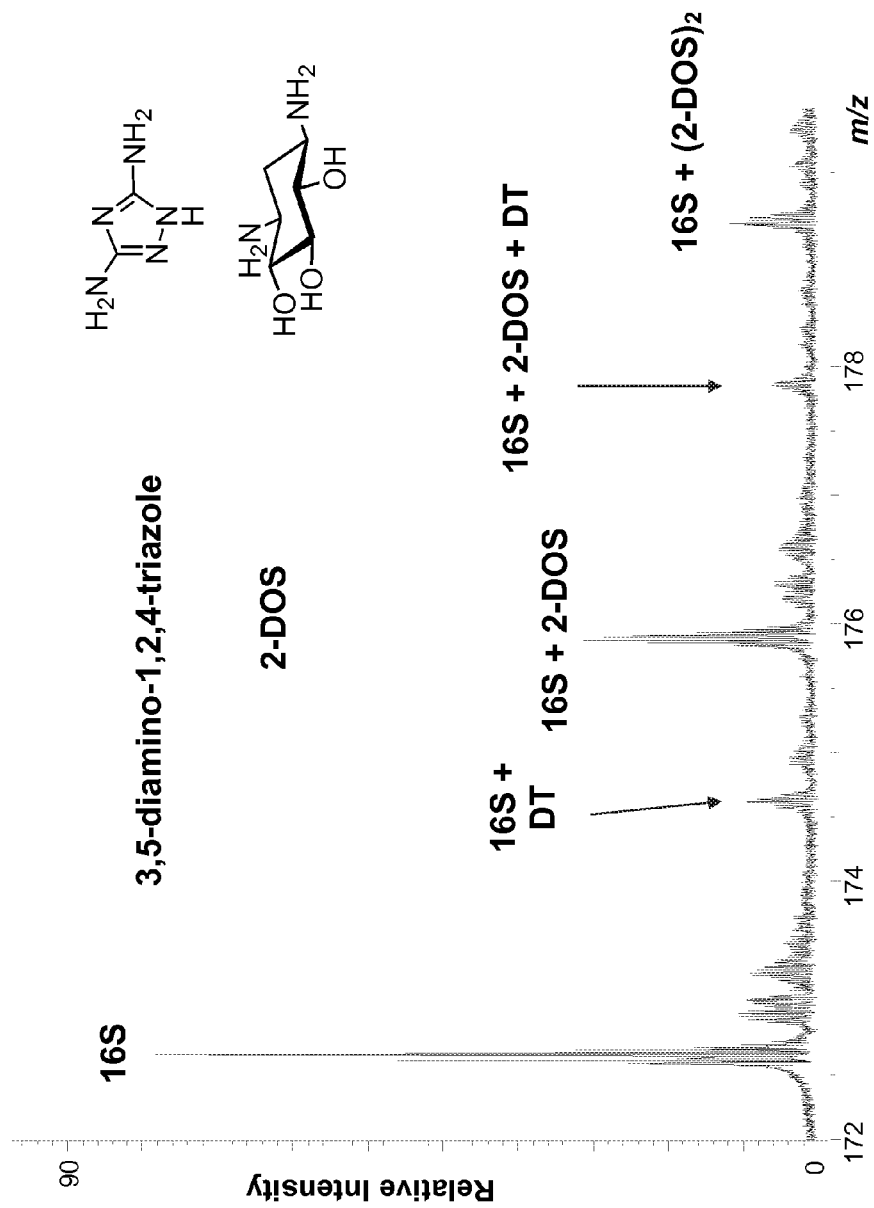
FIG. 4 is a mass spectrum showing the concurrent binding of 2-DOS and 3,5-diamino-1,2,4-triazole to the 16S RNA fragment.

The above method for determining a concurrent binding interaction of two ligands is exemplified in FIG. 4 wherein 3,5-diamino-1,2,4-triazole (DT) and 2-deoxystreptamine (2-DOS) are both ligands for target RNA (a 27-mer fragment of ribosomal RNA comprising the 16S A-site). The mass-spectrum trace shows intensity signals for a ternary complex at approximately 1778 m/z for both ligands bound to the target 16S RNA, a binary complex at about 1758 m/z for 2-DOS bound to 16S RNA, a binary complex at 1746 m/z for DT bound to 16S RNA and another signal at about 1727 m/z for 16S RNA unbound by either ligand. The relative ion abundance of the ternary complex (16S+2–DOS+DT) with respect to the unbound 16S target RNA (16S) is equal, within limits of error, to the sum of the relative ion abundance of the contributing binary complex ((16S+DT)×(16S+2–DOS)) with respect to the unbound target (16S) and the contributing binary complex ((16S+2–DOS)+(16S+DT)) with respect to the unbound target (16S). Expressed in a simplified form of the formula:

$$y \approx (16S+2-DOS+DT) - 2 \times (16S+2-DOS) \times (16S+DT)/16S$$

This indicates a concurrent binding interaction between the two ligands, 2-DOS and DT, for the target 16S RNA. Further, a comparison of the ion abundance of the two binary complexes indicates that 2-DOS has greater binding affinity for the target RNA than DT.

Cooperative Binding

Ligands bind cooperatively when the binding of one ligand to the target enhances the binding of the other, i.e. more of the first ligand will bind to the target in the presence of the second ligand than in its absence. Cooperatively binding ligands may bind to their target at distinct locations. In a mixture containing two cooperatively binding ligands there will be an equilibrium of two binary complexes, a ternary complex and unbound target. The ternary complex is a simultaneous adduction of both ligands to the target. One of the binary complexes is complex of the first ligand bound to the target and the other binary complex is that of the second ligand bound to the target. The ligand having the greater affinity for the target will demonstrate a higher signal intensity for its binary complex with the target compared to the other ligand. Cooperative binding interaction between two ligands is determined according to methods of the invention by analyzing the mixture by mass-spectrometry and comparing the absolute ion abundance of the ternary complex to the sum of the relative ion abundance of the binary complexes contributing to the formation of the ternary complex in the same manner as for concurrent binders. However, in the instance of cooperative binding ligands, the relative ion abundance of the ternary complex (TL1L2/T) is greater than the sum of the relative ion abundances of the contributing binary complexes. Expressed another way, a pair of ligands are concurrent binders for a target if in either of the following equivalent formulae the value of y is greater than zero:

$$y = TL1L2 - TL1 \times \frac{TL2}{T} - TL2 \times \frac{TL1}{T}$$

or $$y = \frac{TL1L2}{T} - 2 \times TL1 \times TL2$$

Mixed Binding

Another scenario can arise when comparing the ion abundances, that is, when the ternary ion abundance is less than the sum of the relative abundances of the contributing binary complexes (i.e. y of the above formulae is less than zero). This indicates a more complex binding situation where there is a combination of interactions resulting from a competitive interaction between the ligands while at the same time another non-competitive interaction (cooperative or concurrent) is also occurring. Stated another way, this indicates a mixed binding mode arising when either or both ligands have more than one binding site on the target that may be detected by a mass-spectrum signal for the multiply bound target. Complex binding interaction of two ligands includes competitive/cooperative, competitive/concurrent, cooperative/concurrent, competitive/cooperative/concurrent or further combinations thereof.

A mixture in which two ligands have both competitive and concurrent binding interactions will exhibit a mass-spec signal for a ternary complex whereas a mixture having only a competitive interaction will exhibit no such signal. A mixture in which two ligands exhibit both a competitive and cooperative interaction will exhibit a mass-spec signal for the ternary complex and the absolute ion abundance for the ternary complex (TL1L2) will be greater than the sum of the relative ion abundance for the contributing binary complexes when the cooperative interaction is predominant. Conversely, the absolute ternary abundance will be less when the competitive interaction is stronger than the cooperative interaction. When there is both competitive and concurrent binding interaction, the absolute ternary ion abundance will be less than the sum of the relative ion abundances for the contributing binary complexes and greater when there is both cooperative and concurrent binding interaction.

A further embodiment of the invention includes methods for determining the relative proximity and orientation of binding sites for a first ligand and a second ligand on a target substrate. The target substrate is exposed to a mixture of the second ligand and at least one derivative compound of the first ligand. Derivative compounds of the first ligand are derivative structures that include the first ligand and have at least one substituent group pendent from the first ligand. The mixture is analyzed by mass spectrometry to identify those first ligand derivatives that inhibits the binding of the second ligand to the target substrate. In this embodiment, the method of determining the mode of binding interaction previously discussed may be used to determine the spatial proximity of ligand binding sites on a target. For example, the knowledge that two ligands are concurrent binders indicates that they have separate and distinct binding sites. In order to determine the distance between these two binding sites, derivatives of one of the ligands are prepared and mixed with the other ligand and the target. The derivatives of the first ligand will have the core chemical structure of the ligand but will also have substituents pending from the structure, the substituents having a diversity of lengths and attachment points to the structure.

A ligand derivative that inhibits the binding of the second ligand to the target, i.e. a derivative that is competitive with the second ligand, provides insight into the proximity and orientation of the binding sites relative to each other. A competitive derivative is identified by mass-spec analysis of the mixture and its particular substituent and attachment point on the parent ligand structure is determined. The point of attachment of the substituent indicates the relative orientation while the length of the substituent indicates the relative proximity of the binding sites. In this way the substituent group serves as a molecular ruler and compass.

An efficient manner of performing the method is by employing combinatorial chemistry techniques to create a library of ligand derivatives having great diversity in substituents. Suitable substituent groups include but are not limited to alkyl (e.g. methyl, ethyl, propyl), alkenyl (e.g. allyl), alkynyl (e.g. propynyl), alkoxy (e.g. methoxy, ethoxy), alkoxycarbonyl, acyl, acyloxy, aryl (e.g. phenyl), aralkyl, hydroxyl, hydroxylamino, keto (=O) amino, alkylamino (e.g. methylamino), mercapto, thioalkyl (e.g. thiomethyl, thioethyl), halogen (e.g. chloro, bromo), nitro, haloalkyl (e.g. trifluoromethyl), phosphorous, phosphate, sulfur and sulfate.

In further embodiment of the invention, the invention includes a screening method for determining compounds having binding affinity to a target substrate. A mixture of the ligands and the target substrate are analyzed by mass spectrometry. First and second ligand that bind to the target substrate are identified. These first and second ligands are concatenated to form a third ligand having greater binding affinity for the target substrate than either first or second ligand. In this embodiment of the invention, ligands are identified using mass spectrometry methods described herein and are concatenated or linked together to form a new ligand incorporating the chemical structure responsible for binding of the two parent ligands to the target. The new concatenated ligand will have greater binding affinity for the target than either of the two parent ligands. An example of this is illustrated in examples 4 and 5 and FIGS. 6-8 where mass-spec analysis of a library of amide compounds revealed two having binding affinity for a fragment of bacterial 16S ribosomal RNA. The two ligands (IBIS-271583 and IBIS-326611) both incorporated a piperazine moiety and a concatenated compound of the two ligands was prepared having a common piperazine moiety from which the remainder of the ligand structures depend. The concatenated compound (IBIS-326645) is shown in FIG. 8 to bind the target 16S RNA fragment with greater affinity (52.4% of the target) than either of the two parent ligands in FIGS. 6 and 7 (27.8% and 14.7% respectively). In a preferred embodiment, the new concatenated ligand comprises the chemical structure of the first and second ligands linked together by a linking group. Suitable linking groups are well known in the art and depend upon the chemical structure of the ligands and are preferably linked to atoms of the ligand molecule not directly involved in binding to the target.

Linking groups are selected that generally are of a length that results in a reduction in entropy of the ligand target system. Typically a linker will have a length of about 15 Angstroms, preferably less than about 10 Angstroms and more preferably less than 5 Angstroms. Preferred linking groups include but are not limited to a direct covalent bond, alkylene (e.g. methylene, ethylene), alkenylene, alkynylene, arylene, ether (e.g. alkylethers), alkylene-esters, thioether, alkylene-thioesters, aminoalkylene (e.g. aminomethylene), amine, thioalkylene and heterocycles (e.g. pyrimidines, piperizine and aralkylene).

Figure 5:
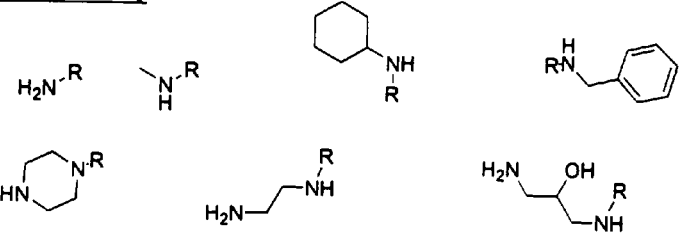
FIG. 5 is a table of particular amines and carboxylic acids that were conjugated at the R group in all combinations to form a library of amide linked compounds. The amide linked compounds were analyzed by mass spectroscopy to determine their binding affinity to 16S RNA fragment.
Figure 5:
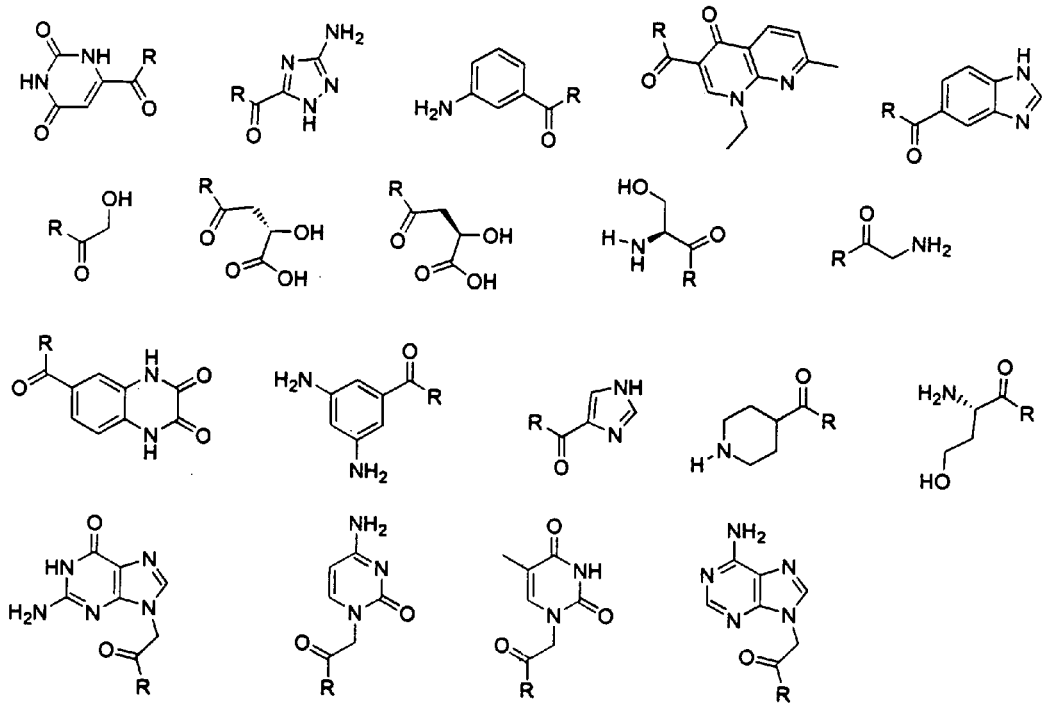
Figure 6:
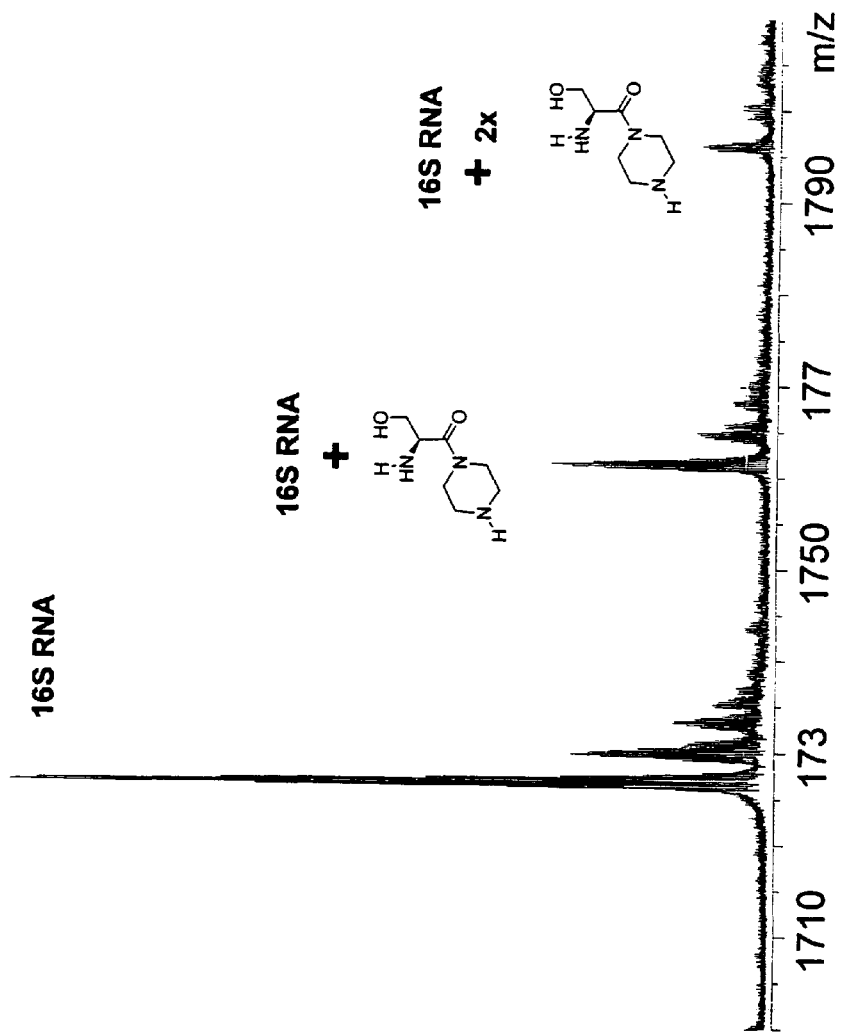
FIG. 6 is a mass spectrum showing the binding of a piperazinyl small molecule IBIS-326611 from the amide library to 16S RNA fragment.
Figure 7:
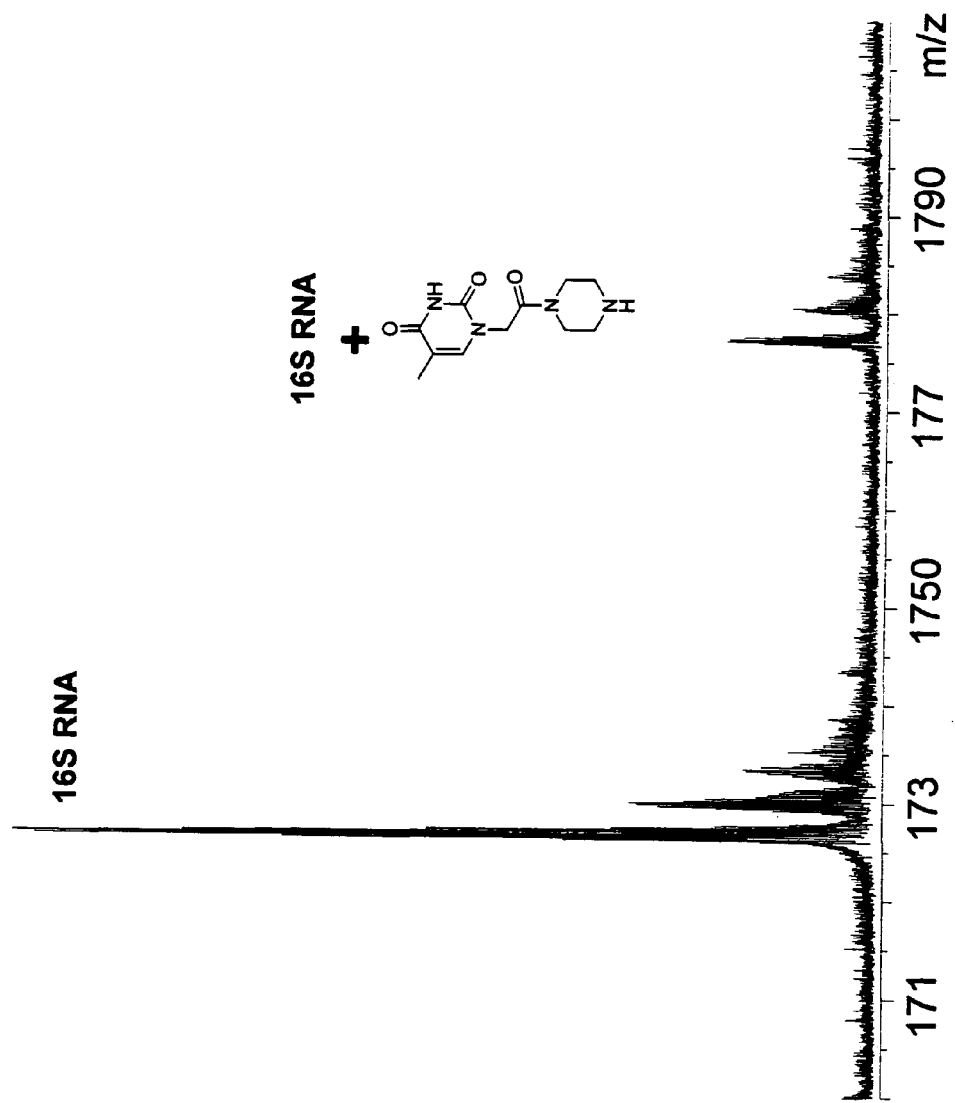
FIG. 7 is a mass spectrum showing the binding to 16S RNA fragment of another piperazinyl small molecule IBIS-326645 from the amide library.
Figure 8:
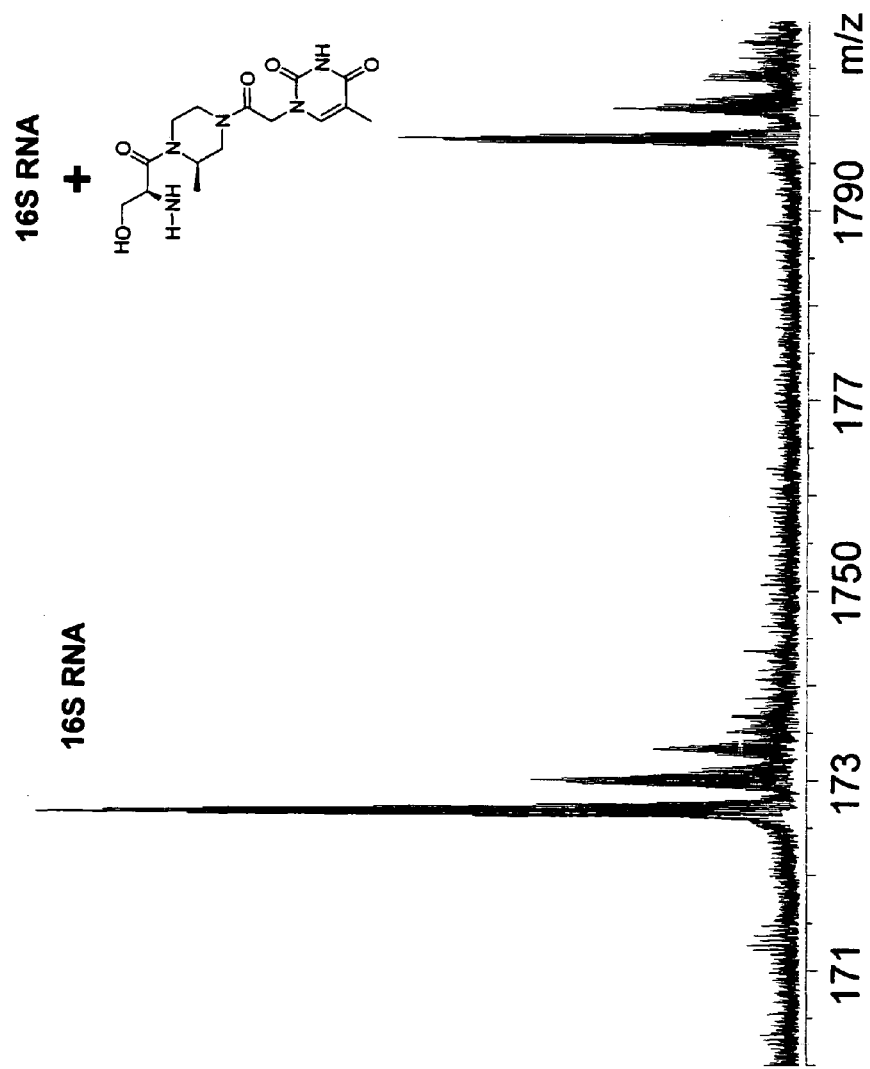
FIG. 8 is a mass spectrum showing the enhanced binding to the 16S RNA fragment of concatenated compound IBIS-271583, derived from the structures of IBIS-326611 and IBIS-326645 and sharing the common piperazine moiety of the two parent compounds. The concatenated compound has greater affinity for 16S than either parent compound.
Figure 9:
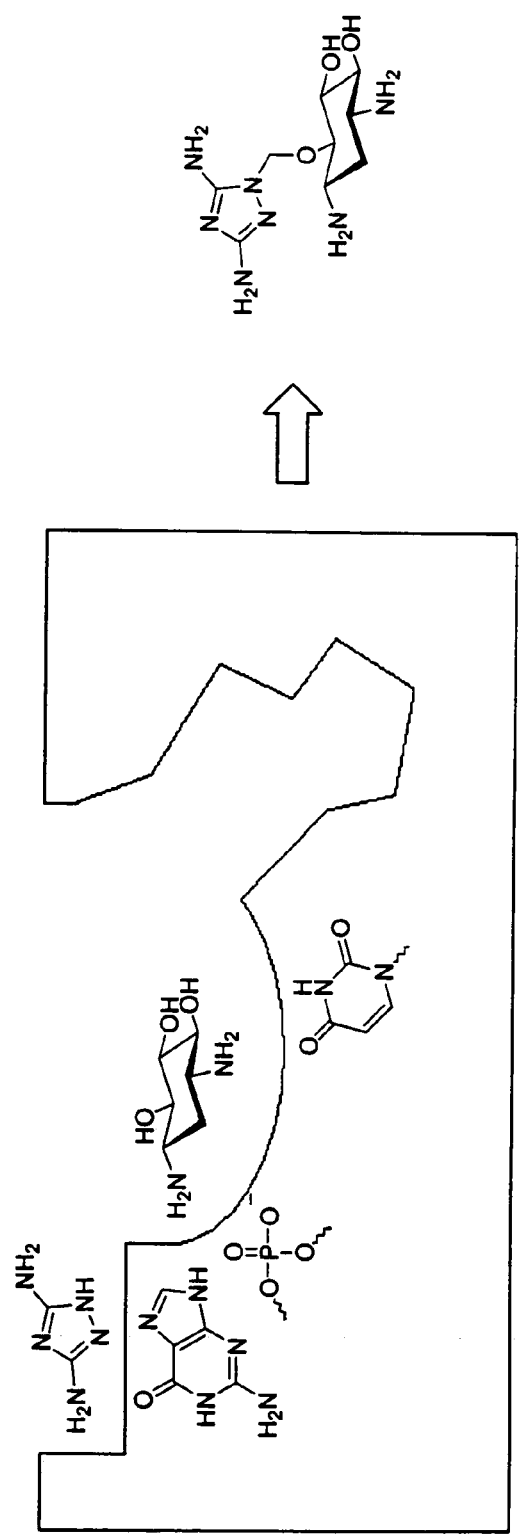
FIG. 9 is a schematic representation of the binding of triazole and 2-deoxystreptamine ligands binding at their respective binding sites on the target 16S RNA fragment and a concatenated compound derived from the two ligands.

An example of the above method is shown in FIGS. 5 through 7. In separate mixtures, 200 µM of three ligands IBIS-326611 ((2S)-2-amino-3-hydroxy-1-piperazinylpropan-1-one), IBIS-326645 (5-methyl-1-(2-oxo-2-piperazinylethyl)-1,3-dihydropyrimidine-2,4-dione) and a concatenated compound thereof, IBIS-271583 (1-{2-[(3R)-4-(2S)-2-amino-3-hydroxypropanoyl)-3-methylpiperazinyl]-2-oxoethyl}-5-methyl-1,3-dihydropyrimidine-2,4-dione) are each mixed with 5 µM of target 16S RNA fragment and analyzed by mass spectrometry. IBIS-326611 is shown in FIG. 5 to form a binary complex having an ion abundance 27.8% that of the unbound 16S RNA while IBIS-326645 in FIG. 6 forms a binary complex having an ion abundance 14.7% that of the unbound 16S RNA. The concatenated compound IBIS-271483 on the other hand forms a binary complex having 52.4% ion abundance relative to unbound 16S RNA, and therefor has greater affinity for the target 16S RNA than either of the parent compounds.

New concatenated ligands may be screened in the same manner as were the parent ligands, and the affinities of those that bind may be measured through titration of the ligand concentration. The binding location of the new molecule on the target may be determined using a mass spectrometry-based protection assay, infrared multiphoton dissociation, NMR, X-ray crystallography, AFM force microcopy and other known techniques. Suitable concatenated ligands having improved affinity may then be screened in functional assays to demonstrate a biological effect appropriate for a drug molecule. If the biological activity is insufficient, the molecules may be iterated through the process additional times.

In a preferred embodiment the linking group is chosen based on the relative orientation and proximity of the ligand binding sites by exposing the target substrate to a mixture of the second ligand and a plurality of derivative compounds of the first ligand wherein the first ligand derivatives comprising the chemical structure of the first ligand and at least one substituent group pending therefrom. The mixture is analyzed by mass spectrometry to identify a first ligand derivative that inhibits the binding of said second ligand to the target substrate. In this method, mass spectrometry is used to infer the local environments of ligands. The footprint of one or more of the binding ligands may be increased through addition of substituents such as methyl, ethyl, amino, methylamino, methoxy, ethoxy, thiomethyl, thioethyl, bromo, nitro, chloro, trifluoromethyl and phenyl groups at different positions. This allows a SAR series to be constructed (either virtually or in vitro) for each individual ligand. For example, a methyl group may be added to the first ligand and it is found by the mass-spec screening that the methyl group does not affect the binding of the second ligand. This suggests that a methyl group may be an appropriate point to use for ligation with the second ligand. For example, it was found that first and second ligands bind cooperatively to a target and that a methyl derivative of the first ligand retains the cooperative binding with the second ligand. This indicates that point of attachment of the methyl group on the first ligand may be a suitable point on that ligand for linking to the second ligand. In the instance where the binding sites of the first and second ligand overlap, a concatenated compound comprising a fusion of the two chemical structures that are responsible for binding to the target will have greater affinity to the target than either first or second ligand.

Alternatively, the orientation and proximity of the binding sites may be determined by molecular modeling techniques, i.e., in silico, using programs such as MCSS (LeClerk, 1999) and others that virtually reproduce stacking, hydrogen bonding and electrostatic contacts with the target. Preferably, orientation and proximity of the binding sites is determined by a combination of molecular modeling and the methods employing derivatized ligands in an iterative process wherein each technique provides information useful in performing the other. For example, molecular modeling may predict the orientation of a ligand at its binding site and give insight into the position at which a substituent or linking group may be attached to the ligand. Other techniques may also be used separately or in combination with those mentioned such as X-ray crystallography which provides 3-dimensional orientation and location when bound to its target. Another technique available for determining orientation and proximity of ligands at their binding site for designing linking groups is by NMR. A particular NMR method for determining orientation and proximity is described in patent application WO97/18469 which claims priority from U.S. Ser. No. 08/558,644 (filed 14 Nov. 1995) and 08/678,903 (filed 12 Jul. 1996) each incorporated herein by reference. In this NMR method a target molecule is labeled with $^{15}N$ and analyzed by $^{15}N/^{1}H$ NMR correlation spectroscopy when bound by the ligands. This method is particularly useful for targets that are easily labeled with $^{15}N$ such as proteins and peptide.

EXAMPLES

General

All MS experiments were performed by using an Apex II 70e ESI-FT-ICR MS (Bruker Daltonics, Billerica, Mass.) with an actively shielded 7 tesla superconducting magnet. RNA solutions were prepared in 50 mM $NH_4OAc$ (pH 7), mixed with 10% isopropanol to aid desolvation, and infused at a rate of 1.5 µL/min by using a syringe pump. Ions were formed in a modified electrospray source (Analytica, Branford, Conn.) by using an off-axis grounded electrospray probe positioned ca. 1.5 cm from the metallized terminus of the glass desolvation capillary biased at 5,000 V. A countercurrent flow of dry oxygen gas heated to 150° C. was used to assist in the desolvation process. Ions were accumulated in an external ion reservoir comprised of a radio frequency-only hexapole, a skimmer cone, and an auxiliary electrode for 1,000 ms before transfer into the trapped ion cell for mass analysis. Each spectrum was the result of the co-addition of 64 transients comprised of 524,288 data points acquired over a 217,391-kHz bandwidth, resulting in a 1.2-sec detection interval. All aspects of pulse sequence control, data acquisition, and postacquisition processing were performed by using a Bruker Daltonics data station running XMASS Version 4.0 on a Silicon Graphics (Mountain View, Calif.) R5000 computer.

Example 1

Mass Spectrometry-Based Selection of Compounds with Affinity for RNA.

RNA binding ligands are selected from a set of compounds using mass spectrometry. The RNA used for the target molecule is an RNA whose electrospray ionization properties have been optimized in conjunction with optimization of the electrospray ionization and desolvation conditions. A set of compounds that contains members with molecular mass less than 200, 3 or fewer rotatable bonds, no more than one sulfur, phosphorous, or halogen atom, and at least 20 mM solubility in dimethylsulfoxide is used. A 50 µM stock solution of the RNA is purified, and dialyzed to remove sodium and potassium ions.

The compound set is pooled into mixtures of 8 members, each present at 1-10 mM in =15 DMSO. A collection of these mixtures is diluted 1:50 into an aqueous solution containing 50-150 mM ammonium acetate buffer at pH 7.0, 1-5 µM RNA target, and 10-50% isopropanol, ethanol, or methanol to create the screening sample. The aqueous solution contains 100 µM each of 8 compounds, 50 mM ammonium acetate, 5 µM RNA target, and 25% isopropanol. These screening samples are arrayed in a 96-well microtiter plate, or added to individual vials for queuing into an automated robotic liquid hander under computer control by the mass spectrometer.

The source voltage potentials are adjusted to give stable electrospray ionization by monitoring the ion abundance of the free RNA. The temperature of the desolvation capillary is next reduced incrementally and the voltage potential between the capillary and the first skimmer lens element of the mass spectrometer is adjusted until adducts of ammonia with them RNA can be observed. If available on the mass spectrometers, the partial gas pressure beyond the desolvation capillary is adjusted by throttling the pumping speed. This gas pressure may also be altered to optimize the ion abundance and observation of the ammonium ion adducts. After instrument performance has been optimized, the voltage potential between the capillary and skimmer lens is increased to reduce the abundance of the ion from the monoammonium-RNA complex to −10% of the abundance of the ion from the RNA. These instrument parameters are used for detection of complexes between the RNA and compound set.

The compound set is screened for members that form non-covalent complexes with the RNA. The relative abundances and stoichiometries of the non-covalent complexes with the RNA are measured from the integrated ion intensities, and the results are stored in a relational database cross-indexed to the structure of the compounds.

Figure 2:
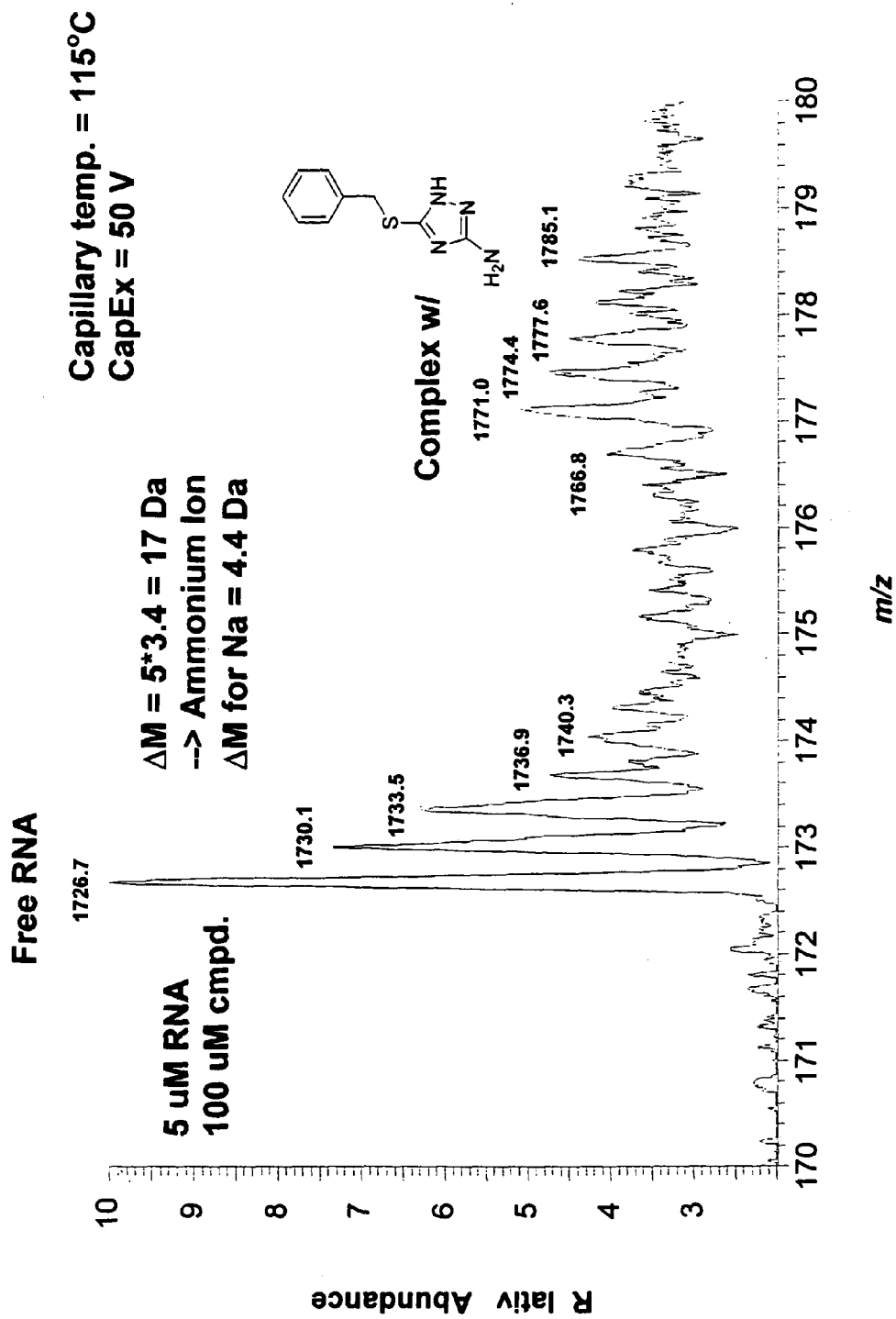
FIG. 2 is a mass spectrum showing binding of a small molecule ligand (2-amino-4-benzylthio-1,2,4-triazole) to a 27-mer fragment of bacterial 16S A-site ribosomal RNA and ammonium as standard ligand.

FIG. 2 shows the resulting spectrum obtained after adjustment of operating performance conditions of the mass spectrometer for detection of weak affinity complexes. Free target RNA is seen at 1726.7 m/z in the spectrum. Ions associated with adducts of ammonium with the RNA target can be observed and are easily differentiated from sodium ion adducts based on the combined molecular mass of the ammonium/RNA adducts. Ions associated with an adduct of a triazole ligand (2-amino-4-benzylthio-1,2,4-triazole) are also seen. The RNA target is present at a concentration 5 micromolar and the triazole ligand at a concentration of 100 micromolar and the relative abundances of the ion peaks are normalized to that of the target RNA.

Example 2

Chemical Optimization of Compounds that Form Complexes with the RNA Target.

In a second step, compounds are obtained with structures derived from those selected in Example 1. These compounds may be simple derivatives with additional methyl, amino, or hydroxyl groups, or derivatives where the composition and size of rings and side chains have been varied. These derivatives are screened as in Example 1 to obtain SAR information and to optimize the binding affinity with the RNA target.

Example 3

Determination of the Mode of Binding for Compounds Forming Complexes with the RNA Target.

In the compound collection used in Example 1, those compounds that formed complexes with the RNA target are pooled into groups of 4-10 and screened again as a mixture against the RNA target as outlined in Example 1. Since all of the compounds have been shown previously to bind to the RNA, three possible changes in the relative ion abundance are observed in the mass spectrometry assay. If two compounds bind at the same site, the ion abundance of the RNA complex for the weaker binder will be decreased through competition for RNA binding with the higher affinity binder (competitive binding). An example is presented in FIG. 3, where the ion abundance from a glucosamine-RNA complex is reduced as glucosamine is displaced from the RNA by addition of a benzimidazole compound. If two compounds can bind at distinct sites, signals will be observed from the respective binary complexes with the RNA and from the ternary complex where both compounds bind to the RNA simultaneously (concurrent binders). If the binding of one compound enhances the binding of a second compound, the ion abundance from the ternary complex will be enhanced relative to the ion abundance from the respective binary complexes (cooperative binding). An example of cooperative binding between 2-deoxystreptamine (2-DOS) and 3,5-diaminotriazole (3,5-DT) is presented in FIG. 4. The relative ion abundance from the secondary complex for 3,5-DT to the free RNA is measured, as is the relative ion abundance from the ternary complex between 3,5-DT, 2-DOS, and RNA and the binary complex. If the ratio of the relative ion abundance is greater than 1, the binding is considered to be cooperative. The ratios of relative ion abundance are calculated and stored in a database for all compounds that bind to this RNA.

Example 4

Amide Library Synthesis—General Procedures

Operations involving resin were carried out in a Quest 210 automated synthesizer (Argonaut Technologies, San Carlos, Calif.). HPLC/MS spectra were obtained on a HP1100 MSD system (Hewlett-Packard, Palo Alto, Calif.) equipped with a SEDEX (Sedere) evaporative light scattering detector (ELSD). A 4.6×50 mm Zorbax XDB-C18 reversed phase column (Hewlett-Packard, Palo Alto, Calif.) was operated using a linear gradient of 5% A to 100% B over 4 min at 2 mL/min flow rate (A=10 mM aqueous ammonium acetate+ 1% v/v acetic acid, B=10 mM ammonium acetate in 95:5 v/v acetonitrile/water+1% v/v acetic acid. The flow was split 3:1 after the column, with 0.5 mL/min flowing to the MSD mass detector, and 1.5 mL/min flowing to the ELSD detector. Quantitation was based on integration of the ELSD peak corresponding to product, which was identified by the corresponding mass spectrum of the eluting peak. $^1$H NMR spectra for all compounds were recorded either at 399.94 MHz on a Varian Unity 400 NMR spectrometer or at 199.975 MHz on a Varian Gemini 200 NMR spectrometer.

General Procedure for Synthesis of Secondary Amine Resins: Preparation of Ag-Mb-Benzylamine Resin 2-methoxy-4-alkoxy-benzaldehyde PEG-PS resin (Argo-Gel-MB-CHO, Argonaut Technologies, San Carlos, Calif., 10 g, 0.4 mmole/g) was slurried in 30 ml dry trimethylorthoformate (TMOF). Benzylamine (0.52 ml, 4.8 mmole) was added and the slurry swirled gently on a shaker table under dry nitrogen overnight. A solution of 40 ml dry methanol, acetic acid (0.46 ml, 8.0 mmole) and borane-pyridine complex (1.0 ml, 8.0 mmole) was added, and the slurry swirled overnight. The resin was filtered, and washed several times with methanol, DMF, $CH_2Cl_2$, and finally methanol. Gel-phase NMR showed complete conversion from the aldehyde to secondary benzylamine derivative. Gel-phase $^{13}$C NMR ($C_6D_6$) δ 40.9, 48.1, 53.0, 54.8, 67.7, 70.9 (PEG linker), 99.5, 104.7, 121.3, 127.0, 127.8 (poly-styrene beads), 128.5, 130.5, 141.2, 159.0, 159.8.

The supports AG-MB-cyclohexylamine and AG-MB-methylamine, were similarly prepared using cyclohexyl and methylamine (used as a methanol solution available from Aldrich), respectively. The following are the resins employed and the resulting amine functionality of the library compounds.

| resin | amine functionality |
| --- | --- |
| 1,2-diaminoethane-PS | 1,2-diaminoethane |
| 2-OH-1,3-diaminopropane-PS | 2-OH-1,3-diaminopropane |
| AG-MB-benzylamine | benzylamine |
| AG-MB-cyclohexylamine | cyclohexylamine |
| AG-MB-methylamine | methylamine |
| AG-Rink-NH-Fmoc | amino |
| PS-trityl-piperazine | piperazine |

General Procedure for Synthesis of Amide Motifs

The desired carboxylic acid (1 eq.) was suspended in dry DMF (5 mL/mmole), and HATU (Perseptive Biosystems, 1 eq.) and collidine (3 eq.) was added. The suspension was stirred for 15 min, and if a suspension still existed, diisopropylethylamine (1 eq.) was added, and stirring continued. At this point all acids were in solution. This 0.2 M (5 eq. per eq. of amine on the resin) solution of activated acid was added to the appropriate resin containing a primary or secondary amine, and the mixture was agitated overnight at 65° C. The resins were either purchased from Novabiochem, Argonaut Technologies, or prepared via the general procedure. The mixture was filtered, and the resin washed with DMF (3×), MeOH (3×), $CH_2Cl_2$ (3×), DMF (3×) and $CH_2Cl_2$ (3×) and dried with a flow of inert gas. To the resulting resin, trifluoroacetic acid (7 mL/g dry resin) containing 5% v/v triisopropylsilane was added, and the suspension agitated for 4 h. The mixture was filtered, and the resin washed with trifluoroacetic acid (3×). The combined filtrates were concentrated to afford the desired products. The products were characterized by HPLC/MS and were generally sufficiently pure for testing.

The following are the carboxylic acids each of which were coupled with each of the resin bound amines listed above. The corresponding amide functionality of the resulting library compounds are listed thereafter.

Carboxylic Acid
(R)-(+2,2-dimethyl-5-oxo-1,3-dioxolane-4-acetic acid
(S)-(+)-2,2-dimethyl-5-oxo-1,3-dioxolane-4-acetic acid
2,3-dihydroxyquinoxaline-6-carboxylic acid
2-N-Bhoc-guanine-1-acetic acid
4-N-Bhoc-cytosine-1-acetic acid
6-N-Bhoc-adenine-1-acetic acid
bis(BOC-3,5-diaminobenzoic acid)
BOC-3-ABZ—OH
BOC-benzimidazole-5-carboxylic acid
BOC-glycine
BOC-imidazole-4-carboxylic acid
BOC-isonipecotic acid
BOC-SER(tBu)-OH
FMOC-3-amino-1,2,4-triazole-5-carboxylic acid
nalidixic acid
N-BOC-L-homoserine
orotic acid
t-butoxyacetic acid
thymine-1-acetic acid
Amide Functionality
(R)-3-hydroxy-3-carboxypropionyl
(S)-3-hydroxy-3-carboxypropionyl
2,3-dihydroxyquinoxaline-6-carboxyl
guanine-1-acetyl
cytosine-1-acetyl
adenine-1-acetyl
3,5-diaminobenzoyl
3-aminobenzoyl
5-carboxy-benzimidazole
1-aminoacetyl
imidazole-4-carboxyl
isonipecotyl
(2S)-2-amino-3-hydroxypropionyl
3-amino-1,2,4-triazole-5-carboxyl
nalidixoyl
(2S)-2-amino-4-hydroxybutyryl
orotyl
hydroxyacetyl
thymine-1-acetyl Example 5

(2S)-2-Amino-3-hydroxy-1-piperazinylpropan-1-one

According to the general procedure, the title compound was prepared using PS-trityl-piperazine resin (Novabiochem) and BOC-(tBu)-Serine (Bachem): HPLC/MS M+H 174 fnd., (0.25 min, 100%)

Thymine-1-acetylpiperazine

According to the general procedure, the title compound was prepared using PS-trityl-piperazine resin (Novabiochem) and thymine-1-acetic acid (Aldrich): HPLC/MS M+H=253 fnd., (0.29 min, 100%).

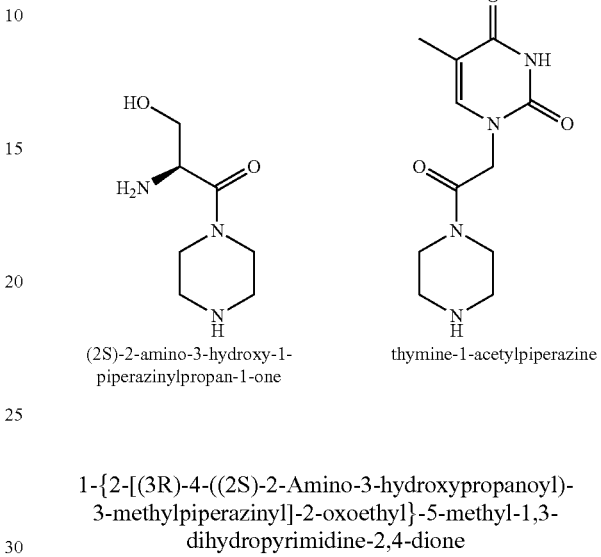

(2S)-2-amino-3-hydroxy-1-piperazinylpropan-1-one thymine-1-acetylpiperazine

1-{2-[(3R)-4-((2S)-2-Amino-3-hydroxypropanoyl)-3-methylpiperazinyl]-2-oxoethyl}-5-methyl-1,3-dihydropyrimidine-2,4-dione HATU (1.1 g, 2.7 mmol) and DIEA (4.7 mL, 27 mmol) were added sequentially to a solution of Boc-Ser(tBu)-OH (0.71 g, 2.7 mmol) in DMF (10 mL). The mixture was stirred at room temperature for about 30 min then was added to a solution of (R)-(−)-2-methylpiperazine (0.3 g, 3 mmol) in DMF (5 mL). The mixture was stirred for 12 h and was diluted with a mixture of sat. NaHCO$_3$/EtOAc (200 mL, v/v, 50:50). The aqueous layer was extracted with more EtOAc (2×30 mL). The combined organic layer was dried (Na$_2$SO$_4$), filtered, and concentrated in vacuo to give a colorless oily residue, which was used in the next step without purification.

HATU (0.38 g, 1.0 mmol) and 2,4,6-collidine (0.73 mL, 5.5 mmol) were added sequentially to a solution of thymine-1-acetic acid (0.19 g, 1 mmol) in DMF (5 mL). The mixture was stirred at room temperature for about 30 min then was added to a solution of the residue prepared above in DMF (5 mL). The mixture was stirred for 12 h and was diluted with a mixture of sat. NaHCO$_3$/EtOAc (100 mL, v/v, 50:50). The aqueous layer was extracted with more EtOAc (2×10 mL). The combined organic layer was dried (Na$_2$SO$_4$), filtered, and concentrated in vacuo to give a colorless oily residue. Purification of the residue by flash column chromatography (gradient elution 3-5% MeOH/CH$_2$CL$_2$) provided N—BOC-O-t-butyl protected derivative (38 mg, 8% yield in two step): TLC (R$_f$=0.4; 10% MeOH/CH$_2$Cl$_2$); $^{13}$CNMR (DMSO-d$_6$) δ 169.8, 165.4, 164.4, 155.2, 151.0, 142.2, 107.9, 78.2, 72.7, 61.5, 50.3, 48.2, 45.1, 28.1, 27.1, 11.8; HRMS (MALDI) m/z 532.2736 (M+Na)$^+$ (C$_{24}$H$_{39}$N$_5$O$_7$ requires 532.2747).

A solution of the protected derivative (23.4 mg, 0.046 mmol) in concentrated aqueous HCl (2 mL) was stirred at room temperature for 12 h. The reaction mixture was evaporated to give the title compound (20 mg, quantitative yield). $^{13}$C NMR (CD$_3$OD) δ 167.3, 167.0, 153.2, 143.9, 111.0, 73.6, 72.4, 62.2, 60.8, 54.4, 47.1, 46.5, 43.8, 12.3.

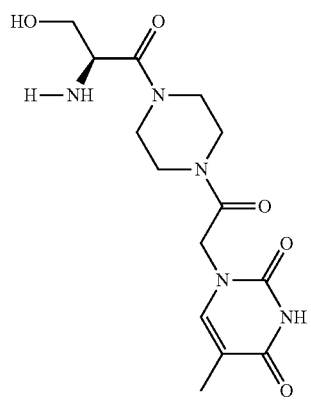

Example 6

2-Deoxy-1,3-diazido-4-[(5-bromo-3-nitro-1,2,4-triazolyl)methyl]-5,6-di-O-acetylstreptamine Dry hydrogen chloride is passed through a solution of 2-deoxy-1,3-diazido-5,6-di-O-acetylstreptamine (296 mg, 1 mmole, prepared according to the method of Wong et. al., *J. Am. Chem. Soc.* 1999, 121, 6527-6541) and paraformaldehyde (45 mg, 1.5 mmole) in dichlorethane at 0° C. for 6 h. Solid $CaCl_2$ is added, the mixture filtered, then concentrated in vacuo. The syrup is azeotroped three times with dry acetonitrile to provide the chloromethyl derivative. Separately, a suspension of 5-bromo-3-nitro-1,2,4-triazole (386 mg, 2 mmole) is stirred with sodium hydride (60% w/w, 80 mg, 2 mmole) for 0.5 h in acetonitrile (20 mL). This suspension is then added directly to the chloromethyl derivative, and the mixture stirred overnight at room temperature. Water and ethyl acetate were added, the organic layer collected, dried over magnesium sulfate, concentrated, and chromatographed (20% ethyl acetate/hexanes) to provide the title compound.

2-Deoxy-1,3-diazido-4-[(5-amino-3-nitro-1,2,4-triazolyl)methyl]streptamine

2-Deoxy-1,3-diazido-4-[5-bromo-3-nitro-1,2,4-triazolyl)methyl]-5,6-di-O-acetylstreptamine is dissolved in 3:1 dioxane/28% aqueous ammonia, and the solution stirred at 60° C. in a sealed vessel overnight. The solvent is removed, and the residue chromatographed (10% methanol/chloroform) to provide the title compound.

2-Deoxy-4-[(3,5-diamino-1,2,4-triazolyl)methyl]streptamine

2-Deoxy-1,3-diazido-4-[(5-amino-3-nitro-1,2,4-triazolyl)methyl]streptamine is dissolved in ethanol, and hydrogenated over 10% palladium on carbon catalyst at 50 psi with shaking for 72 h. The mixture was filtered through celite, and the solvent removed to afford the title compound.

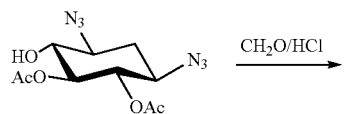

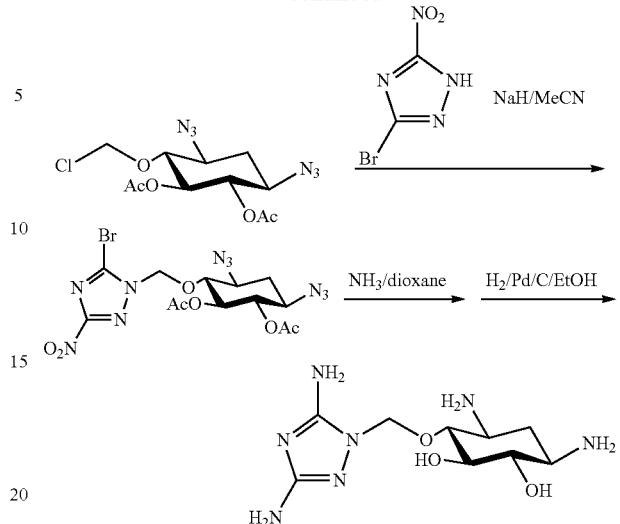

Example 7

ESI and CAD Mass Spec Analysis of Binding of 2-Deoxystreptamine (2-DOS) to 16S Ribosomal RNA Fragment.

2'-O-ACE protected 27mer RNA (GGCGUCACACCU-UCGGGUGAAGUCGCC; SEQ ID NO:1) was purchased from Dharmacon Research (Boulder, Colo.). Aqueous solutions were deprotected for 30 min at 60° C. in a 0.1M tetramethylenediamine acetate buffer at pH 3.5. The resulting solution was evaporated to dryness under reduced pressure and a stock RNA solution (80 μM) was prepared in 50 mM ammonium acetate buffer, pH 7.0. All chemicals were purchased from Aldrich Chemicals (Milwaukee), except for 2-deoxystreptamine and 3,5-diamino-1-N-methyl-triazole, which were prepared according to Georgiadis et al (J. Carbohydr. Chem. 1991, 10, 739-748) and Kaiser et al (U.S. Pat. No. 2,648,670). Ligands were added to the indicated final concentrations from 20 mM aqueous solutions. Final RNA concentrations of 5 μM were prepared by dilution with 50 mM ammonium acetate buffer, pH 7.0, and 30% isopropyl alcohol added to assist the desolvation process.

Mass spectrometry experiments were performed with an LCQ quadrupole ion trap mass spectrometer (ThermoQuest; San Jose, Calif.) operating in the negative ionization mode and with a 7.0 Tesla Apex 11e Fourier Transform Ion Cyclotron Resonance (FTICR) mass spectrometer (Bruker, Billerica, Mass.). For the LCQ mass spectrometer, the electrospray needle voltage was adjusted to −3.5 kV and the spray was stabilized with a sheath gas pressure of 50 psi and an auxiliary gas pressure of 20 psi (60:40 $N_2:O_2$). The sample was introduced at 2.5 μL/min and the capillary interface heated to a temperature of 180° C. The He gas pressure in the ion trap was held at 1 mTorr (uncorrected). MS/MS experiments on the LCQ employed a 1.5 Da isolation window having the desired m/z. Ions were selected via resonance ejection and stored with q=0.2. The excitation RF voltage was applied to the end caps for 30 msec and increased stepwise over the specified range (0.2-1.6 $V_{pp}$). A total of 64 scans comprised of 8 microscans were summed over m/z 1600-2000 following ion trapping for ~200 msec.

Identical sample preparations were used for experiments with FTICR mass spectrometer. The electrospray needle voltage was adjusted to −4.0 kV and the spray was stabilized with a gas pressure of 45 psi (50:50 $N_2:O_2$). Sample was introduced at 1.0 µL/min and the capillary interface unheated. Ions were stored for 1.25 sec in a hexapole ion guide prior to transfer to the trapped ion cell. The indicated gas pressure over the vacuum pump situated below the hexapole ion guide was ~$8\times10^{-6}$ mbar. The parallel measurements of relative activation energy were performed with the FTICR mass spectrometer by varying the potential difference between the capillary exit and the first skimmer lens element. Typically, 32 1.2 sec transients of 512 k data points were summed prior to Fourier transformation and display.

QXP software was used to determine the optimal geometry of ligand-target RNA complex wherein the RNA was held fixed and the ligand treated as completely flexible. The QXP method employed a Monte Carlo perturbation method in conjunction with energy minimization to explore the conformational space in a robust manner. QXP used a modified version of the AMBER force field with a distance-dependent dielectric of 4.0*r (Weiner et al., *J. Am. Chem. Soc.* 1984, 106, 765).

The formal charges on the phosphate oxygen atoms were scaled down by 80% to account for the absence of explicit solvent molecules or counterions in the calculations. During the search process, a random translational movement between 0.5 and 15 Å was given to the ligand.

The solution structure of gentamycin-16S RNA, as determined by using NMR technique, was used in docking calculations (PDB entry 1BYJ). At the start of the calculation, gentamycin was pulled outside the pocket and all the torsions were randomized. Docking searches using QXP resulted in rms difference between the lowest energy docked structure and the energy-minimized NMR structure of less than 0.5 Å. Good correlation between the rms deviation and QXP scores was observed.

Figure 10:
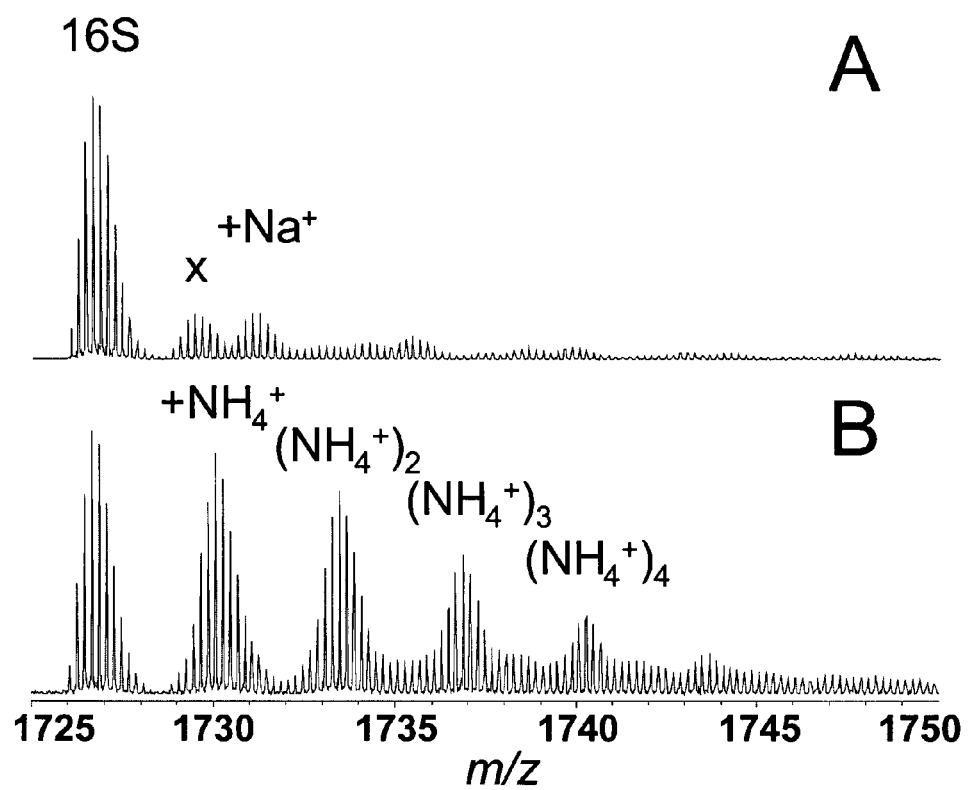
FIG. 10 is a mass spectrum of ammonium ion adducts of 16S as a function of desolvation conditions. (A) No ammonium adducted ions observed at a −180 V cap exit-skimmer potential. Two smaller higher mass signals from a methylated impurity in the RNA (x; M+14.016 Da) and sodium-adducted species (Na; M+21.982 Da) respectively. (B) At a −115 V cap exit-skimmer potential, a series of peaks from ammonia-adducted ions are observed at 17.030 Da intervals.

We used the intensity of 16S:ammonium ion complexes as a measure of the "harshness" of the ESI and desolvation processes for RNA targets and their complexes. As shown in FIG. 10 (A), the FTICR source with an unheated desolvation capillary and a −165 V capillary-skimmer potential lead to complete desolvation of 16S with concomitant dissociation of bound ammonium ions. Ions with adducted sodium and potassium cations that were not-released during desolvation appeared at higher m/z values. Decreasing the capillary-skimmer potential to −115 V generated the spectrum shown in FIG. 10 (B). The identity of the ammonium ion adducts could be established unambiguously from accurate measurement of the mass difference ($\Delta$ m/z=3.406±0.001) relative to the $[M-5H^+]^{5-}$ ions of 16S. Residual waters had been removed, but a series of ammonium-adducted species were observed at 3.4 m/z intervals. Under these conditions, non-covalent complexes stabilized by a single hydrogen bond were observed. In a similar manner, lowering the desolvation capillary temperature from 180° C. to 125° C. and increasing the capillary-skimmer potential difference from −25 to −45 V generated ammonium-adducted ions of 16S on the quadrupole ion trap mass spectrometer (with lower resolution).

Figure 12:
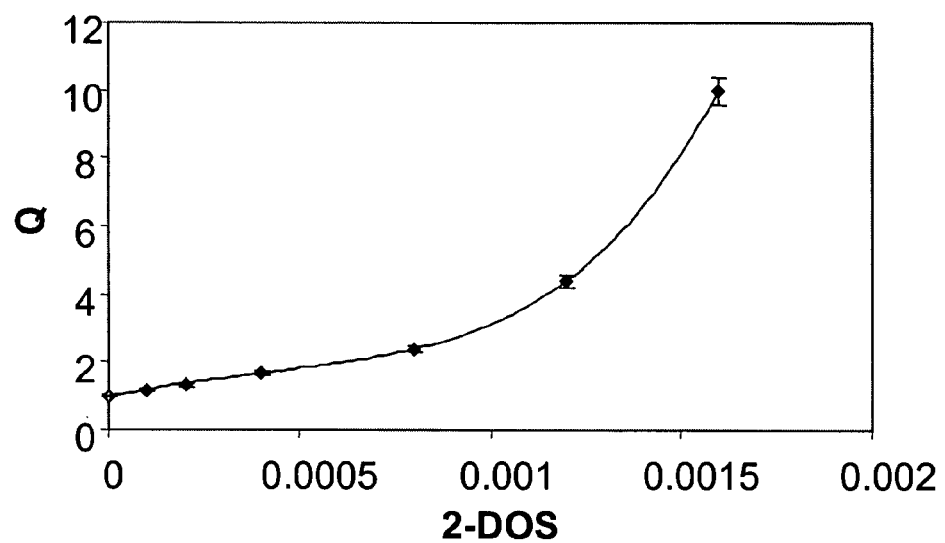
FIG. 12 is a graph showing polynomial fit of Q (the sum of the ion intensities from 16S and all 2-DOS:16S complexes divided by the intensity of 16S) versus 2-DOS concentration (M) in the presence of 100 mM ammonium acetate buffer. The calculated $K_D$ values for 2-DOS, $(2\text{-DOS})_2$, and $(2\text{-DOS})_3$ were 0.6, 1.4, and 4 mM respectively.

2-deoxystreptamine (2-DOS) bound to 16S at multiple locations as a function of increasing concentration. At 0.33 mM, one 2-DOS bound 16S, generating an $[M-5H^+]^{5-}$ complex observed at m/z 1758.9. Complexes corresponding to three and four 2-DOS molecules bound concurrently to 16S appeared at concentrations above 3.3 mM. Knowledge of the binding stoichiometry lead to the use of a fourth-order polynomial for calculation of the respective dissociation constants ($K_D$) (Greig et al., *J. Am. Chem. Soc.* 1995, 117, 10765-10766). As shown in FIG. 12, the 2-DOS binding data fit to the $4^{th}$ order polynomial ($R^2$=0.99), with estimated $K_D$ values of 0.61±0.08 mM, 1.4±0.1 mM, and 4±1 mM.

Figure 13:
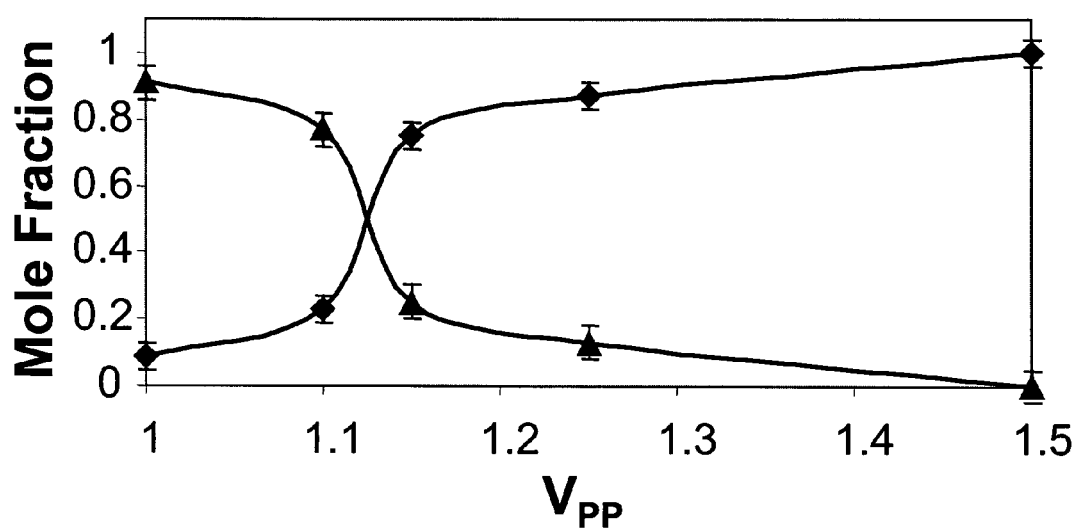
FIG. 13 is a graph showing effective dissociation energy versus mole fraction of ions observed from undissociated (2-DOS):16S complex (▲) and free 16S (♦).
Figure 14:
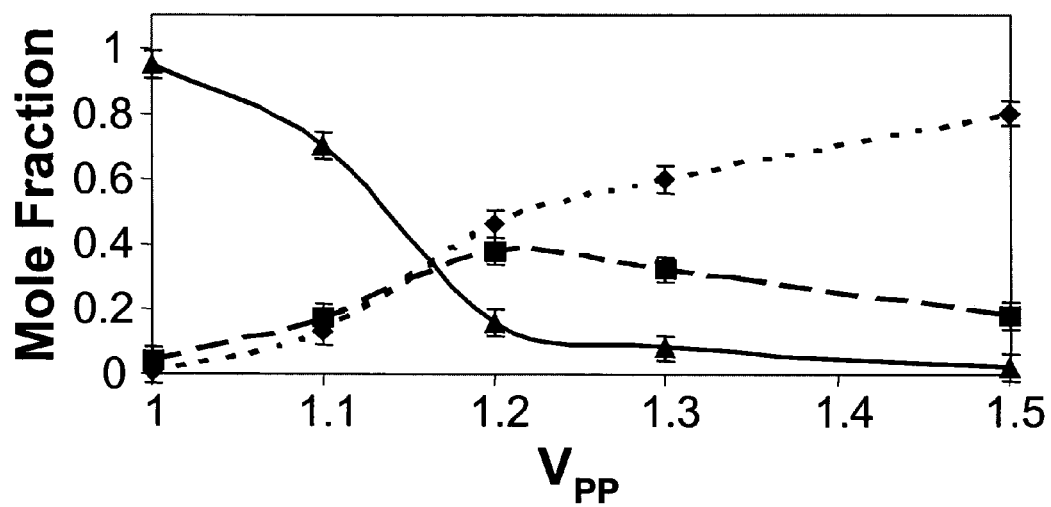
FIG. 14 is a graph showing effective dissociation energy versus mole fraction of ions observed from undissociated bis-(2-DOS):16S (▲; solid), (2-DOS):16S (■; long dash) and 16S (♦; short dash), respectively.

The nature of the binding of 2-DOS at two different sites on 16S was investigated using collisionally activated dissociation (CAD) and MS/MS. CAD of ions from the 2-DOS:RNA complex at m/z 1758.9 yielded ions from unbound 16S. As the relative dissociation energy was increased (FIG. 13) the complex was dissociated into free 16S ions and 2-DOS, with 1.13 V yielding 50% dissociation ($E_{50}$). Next, we studied the CAD of the bis-(2-DOS):16S complex at m/z 1791.4. As shown in FIG. 14, the $E_{50}$ of the bis-(2-DOS):16S complex was also 1.13 V, but the product ions were composed of both free 16S and the (2-DOS):RNA complex. The abundance of the resulting (2-DOS):16S complex increased as the power was increased to 1.21 V, and then started to decrease at higher activation energies, with free 16S ions as the major product. We investigated the stability of the (2-DOS):16S complex generated from the bis-(2-DOS):16S complex in an MS/MS/MS experiment. First, the (2-DOS):16S complex product was isolated following CAD of the bis-(2-DOS):16S complex. These ions were then subjected to additional CAD at different activation energies. The conversion of the (2-DOS):16S complex to free 16S ions was abrupt relative to FIG. 13, with an $E_{50}$ of 1.17 V. In contrast to the ions which started as a (2-DOS):16S complex, complete dissociation of the (2-DOS):16S ions generated from the bis-(2-DOS):16S complex occurred at 1.3 V.

Potential binding sites for 2-DOS on 16S have been investigated using molecular modeling. Leclerc et al., (*Theor. Chem. Acc.* 1999, 101, 131-137) suggested the preferred binding site for 2-DOS on 16S was near the site where the 2-DOS ring binds as part of neomycin-class aminoglycosides. We used QXP, a Monte Carlo-based conformational search algorithm to locate the binding sties for 2-DOS on the RNA using random initial coordinates. We observed two high-probability binding sites corresponding to the location of the 2-DOS ring in neomycin-class aminoglycosides and at the location of the L-idose ring in paromomycin that has been determined by NMR spectroscopy (Fourmy et al., *Science* (Washington, D.C.) 1996, 274, 1367-1371). Additional higher energy binding sites were observed along the wall of the major groove generated by the bulged A1492 and A1493 residues.

Example 8

Determination of Binding Interaction of Deoxystreptamine (2-DOS) and 3,5-Diaminotriazole (3,5-DT) with Target 16S Ribosomal RNA Fragment.

Figure 11:
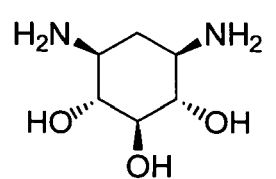
FIG. 11 illustrates structures of ligands analyzed for binding to 16S ribosomal RNA.
Figure 11:
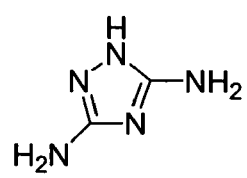
Figure 11:
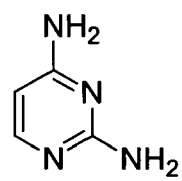
Figure 11:
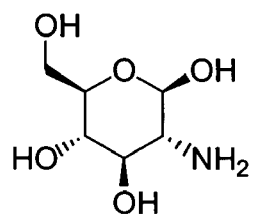
Figure 11:
Figure 11:
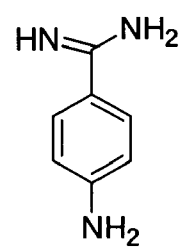
Figure 11:
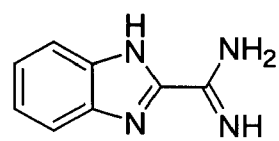

Mass spectrometry assay was used to identify other ligands that bind to 16S with low affinity. The compounds 3,5-diaminotriazole (3,5-DT) and 2,4-diaminopyrimidine (DAP, FIG. 11) bind 16S with ~mM affinities. In a subsequent step, pairs of ligands were mixed with 16S and ESI-MS was used to study the stoichiometry of the resulting complexes. A solution containing 5 µM 16S and 100 µM 2-DOS was mixed with 0.5 mM 3,5-DT. ESI-MS produced signals from free 16S, (3,5-DT):16S, and (2-DOS):16S (FIG. 4). An additional signal was observed from the ternary complex formed between 16S and the two low affinity ligands (2-DOS and 3,5-DT) at m/z 1778.5. The formation of this ternary complex is consistent with simultaneous, concurrent binding of both ligands at different locations on the RNA surface. In addition, a ternary complex was observed at m/z 1791 produced by concurrent binding of two 2-DOS ligands. Binding of 3,5-diamino-1-N-methyltriazole to 16S was not observed by ESI-MS at the ligand concentrations employed. That the addition of a methyl group at N1 is sufficient to preclude binding of the 3,5-DT to 16S suggests a hydrogen bond from N1 is required for binding of the 3,5-DT, or binding occurs at a sterically limited site on 16S. In contrast, aminoalkyl 3,5-DT derivatives complexed to 16S with affinities similar to 3,5-DT. In contrast to the concurrent binding observed with 2-DOS and 3,5-DT, only signals from 2-DOS:16S complexes were observed when 2,4-diaminopyrimidine and 2-DOS were mixed with 16S. The lack of a signal from the ternary complex suggests that their preferred sites overlap and 2-DOS displaces DAP for binding.

Example 9

Determination of Relative Gas Phase Activation Energies ($E_A$) for Dissociation of a Series Ligand-16S Complexes.

The relative gas-phase activation energies ($E_A$) for dissociation of a series of ligand-16S complexes was determined using the FTICR mass spectrometer. The relative ion abundances for a series of complexes between 16S and ammonia, glucosamine (GA), 4-aminoimidazole-5-carboxamide (AICA), DAP, 4-aminobenzamidine (ABA), 2-guanidylbenzimidazole (GBI) (FIG. 11), as well as a series of their ternary complexes was measured as a function of the voltage difference between the capillary exit and the skimmer cone. In each case, a plot of the natural logarithm of the ion abundance versus the dissociation potential was linear with $R^2=0.994$-$0.02$. The slopes were normalized to the $E_A$ for ammonia, and are listed in Table 1 below. The relative gas-phase $E_A$ for AICA, DAP, and GBI were 2.04, 2.16, and 2.12, respectively. The $E_A$ for GA and ABA were 2.86 and 4.00. The order of GA:AICA:16S complex was consistent with the observed product ions where GA or GA and AICA were displaced from 16S. This result suggests that the AICA may lie deeper in the binding pocket than GA, and dissociation from the ternary complex may be blocked. Alternatively, binding of GA may induce a change in the conformation of the RNA that traps the lower affinity ligand.

TABLE 1

Relative activation energies and solution affinities for a series of ligand:16S complexes.

| Compound | Relative $E_A$ | Relative Soln. Affinity |
| --- | --- | --- |
| $NH_3$ | 1.00[a] | |
| 2,4-Diaminopyrimdine | 2.16 ± 0.11 | .17 + 0.04 |
| 4-Aminoimidazolecarboxamide | 2.04 ± 0.16 | .26 + 0.04 |
| Glucosamine | 2.86 ± 0.21 | .86 + 0.03 |
| 2-Guanylbenzimidazole | 2.12 ± 0.09 | .99 + 0.02 |
| 4-aminobenzamidine | 4.00 ± 0.28 | 1.00[b] |

[a]All activation energies have been normalized to the activation energy for loss of ammonia
[b]All solution affinities have been normalized to the solution affinity of 4-aminobenzamidine

SEQUENCE LISTING

<160> NUMBER OF SEQ ID NOS: 1

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence: 16S
      ribosomal RNA fragment

<400> SEQUENCE: 1
ggcgucacac cuucggguga agucgcc                                   27 these values correlated with the solution affinities except for GA, whose solution affinity for 16S was lower than GBI. The increase in gas phase stability for the GA-16S complex may result from additional H-bond contacts between hydroxyl groups and 16S.

The relative $E_A$ for several ternary complexes were also measured using the FTICR mass spectrometer. The GBI:ABA:16S complex dissociated with the $E_A$ of the weaker GBI ligand. However, the $E_A$ for the GA:AICA:16S and GA:DAP:16S complexes were equal to the higher $E_A$ of the GA:16S complex, rather than the lower $E_A$ of the AICA or DAP complexes. The products from gas-phase dissociation of the GA:AICA:16S and GA:GA:16S ternary complexes were measured using the LCQ mass spectrometer. Isolation and CAD of the GA:GA:16S complex yielded GA:16S and 16S in a 3:1 ratio at 50% dissociation. Isolation and CAD of the GA:AICA:16S complex yielded AICA:16S and 16S in a 1:1 ratio at 50% dissociation. Hence, the higher $E_A$ for he

What is claimed is:

1. A method for identifying at least one ligand having an affinity for an RNA target molecule that is equal to or greater than a baseline affinity comprising:
    mixing an amount of ammonium with an excess amount of the RNA target molecule such that unbound RNA target molecule is present in the mixture;
    introducing the mixture of ammonium and RNA target molecule into a mass spectrometer;
    adjusting the mass spectrometer desolvation conditions such that the signal strength of the ammonium bound to the RNA target molecule is from 1% to about 30% of the signal strength of unbound RNA target molecule;
    introducing at least one ligand into a test mixture of the RNA target molecule and the ammonium;
    introducing the test mixture into the mass spectrometer; and
    identifying any complexes of the ligand and the RNA target wherein the ligand has greater than the baseline affinity for the RNA target molecule by discerning those signals that have a signal strength greater than the background noise of the mass spectrometer.

2. The method of claim 1 wherein the mass spectrometer is an electrospray mass spectrometer.

3. The method of claim 1 wherein the baseline affinity expressed as a dissociation constant is about 50 millimolar.

4. The method of claim 2 wherein the electrospray mass spectrometer includes a desolvation capillary and a lens element; and
the adjustment of mass spectrometry desolvation conditions includes adjustment of the voltage potential across the capillary and the lens element.

5. The method of claim 4 wherein the adjustment of mass spectrometry desolvation conditions further includes adjustment of source voltage potential to give a stable electrospray ionization as monitored by the ion abundance of free RNA target molecule.

6. The method of claim 4 wherein the adjustment of mass spectrometry desolvation conditions further includes adjustment of the temperature of the desolvation capillary or countercurrent heating gas.

7. The method of claim 4 wherein the adjustment of mass spectrometry desolvation conditions further includes adjustment of the operating gas pressure within the mass spectrometer downstream of the desolvation capillary.

8. The method of claim 4 wherein the adjustment of the voltage potential across the capillary and the lens element generates an abundance of an ion from a monoammonium-RNA complex to from about 10% to about 20% of the abundance of the ion from target RNA.

9. The method of claim 1 wherein the target RNA is from about 10 to about 200 nucleotides in length.

10. The method of claim 1 wherein the target RNA is from about 15 to about 100 nucleotides in length.

11. The method of claim 1 wherein the target RNA comprises an isolated or purified portion of a larger RNA molecule.

12. The method of claim 1 wherein the target RNA has secondary and ternary structure.

13. The method of claim 1 further including selecting the electrospray mass spectrometer as a mass spectrometer having a gated ion storage device for effecting thermolysis of the test mixture in the mass spectrometer.

14. The method of claim 2 wherein the mass spectrometer includes mass analysis by quadrupole, quadrupole ion trap, time-of-flight, FT-ICR or hybrid mass detectors.

15. The method of claim 2 wherein the electrospray mass spectrometer includes Z-spray, microspray, off-axis spray or pneumatically assisted electrospray ionization.

16. The method of claim 15 wherein the Z-spray, microspray, off-axis spray or pneumatically assisted electrospray ionization each further include countercurrent drying gas.

17. The method of claim 1 further including storing the relative abundance and stoichiometry of said complexes of said ligand and target in a relational database that is cross-indexed to the structure of said ligand.

18. The method of claim 1 wherein the ligand is a member of a set of ligands.

19. The method of claim 18 wherein each of the members of the set of ligands, independently, has a molecular mass less than about 1000 Daltons and has fewer than 15 rotatable bonds.

20. The method of claim 18 wherein each of the members of the set of ligands, independently, has a molecular mass less than about 600 Daltons and has fewer than 8 rotatable bonds.

21. The method of claim 18 wherein each of the members of the set of ligands, independently, has a molecular mass less than about 200 Daltons, has fewer than 4 rotatable bonds, or no more than one sulfur, phosphorous or halogen atom.

22. The method of claim 1 wherein the signal strength is measured by the relative ion abundance.

23. The method of claim 1 including a plurality of target molecules.

24. The method of claim 23 including a plurality of reference compounds.

25. The method of claim 2 wherein the electrospray mass spectrometer includes a desolvation capillary or countercurrent gas and a lens element.

26. A method for identifying at least one ligand having an affinity for an RNA that is equal to or greater than a baseline affinity comprising:
selecting an ammonium ion that forms a non-covalent binding complex with said RNA;
mixing an amount of said ammonium ion with an excess amount of said RNA such that unbound RNA is present in said mixture;
introducing said mixture of said ammonium ion and said RNA into an electrospray mass spectrometer, wherein said electrospray mass spectrometer includes a desolvation capillary and a lens element;
adjusting the electrospray mass spectrometer desolvation conditions such that the signal strength of said ammonium ion bound to said RNA is from 1% to about 30% of the signal strength of unbound RNA, wherein said adjusting desolvation conditions comprises adjustment of the voltage potential across said capillary and said lens element generates an abundance of an ion from a monoammonium-RNA complex to from about 10% to about 20% of the abundance of the ion from target RNA;
introducing at least one ligand into a test mixture of said RNA and said ammonium ion;
introducing said test mixture into said electrospray mass spectrometer; and
identifying any complexes of said ligand and said RNA wherein said ligand has greater than said baseline affinity for said RNA by discerning those signals that have a signal strength greater than the background noise of the electrospray mass spectrometer.

* * * * *